United States Patent
Howling et al.

(10) Patent No.: US 9,005,303 B2
(45) Date of Patent: Apr. 14, 2015

(54) KNEE AND SHOULDER JOINT PROSTHESIS

(75) Inventors: Graeme I. Howling, Leeds (GB); Michael Dean Hughes, Cordova, TN (US); Jeffrey N. Yeager, Nesbit, MS (US); Malcolm Brown, Otley (GB); Rhianna Moss, York (GB); Mason James Bettenga, Memphis, TN (US); Horacio Montes De Oca Balderas, York (GB)

(73) Assignee: Smith & Nephew, Inc., Memphis, TN (US)

( * ) Notice: Subject to any disclaimer, the term of this patent is extended or adjusted under 35 U.S.C. 154(b) by 693 days.

(21) Appl. No.: 12/596,658

(22) PCT Filed: Apr. 16, 2008

(86) PCT No.: PCT/US2008/060406
§ 371 (c)(1),
(2), (4) Date: May 17, 2010

(87) PCT Pub. No.: WO2008/130956
PCT Pub. Date: Oct. 30, 2008

(65) Prior Publication Data
US 2010/0222889 A1    Sep. 2, 2010

Related U.S. Application Data

(60) Provisional application No. 60/912,740, filed on Apr. 19, 2007, provisional application No. 60/912,693, filed on Apr. 19, 2007, provisional application No. 60/988,640, filed on Nov. 16, 2007.

(51) Int. Cl.
*A61F 2/46* (2006.01)
*A61F 2/30* (2006.01)
(Continued)

(52) U.S. Cl.
CPC ............... *A61F 2/40* (2013.01); *A61F 2/30734* (2013.01); *A61F 2/38* (2013.01); *A61F 2002/30092* (2013.01); *A61F 2002/30579* (2013.01); *A61F 2210/0014* (2013.01)

(58) Field of Classification Search
CPC .................. A61F 2/389; A61F 2/3859; A61F 2002/30754; A61F 2002/30878; A61F 2002/30563; A61F 2002/2825; A61F 2002/2892; A61F 2002/30579; A61F 2002/4205; A61F 2/30734
USPC ......................... 623/13.12–13.2, 20.14–20.36
See application file for complete search history.

(56) References Cited

U.S. PATENT DOCUMENTS 3,856,905 A    12/1974    Dawson
3,926,459 A    12/1975    Pontigny
(Continued)

FOREIGN PATENT DOCUMENTS

DE    1604403 B1    11/1970
DE    3036611 A1    6/1982
(Continued)

OTHER PUBLICATIONS

International Search Report mailed Aug. 7, 2009, which was received in corresponding application No. PCT/US2008/060821, 11 pages.
(Continued)

*Primary Examiner* — David Isabella
*Assistant Examiner* — Ann Schillinger
(74) *Attorney, Agent, or Firm* — Krieg DeVault LLP

(57) ABSTRACT

The present disclosure relates to prosthetic knee implants (100), components (101,102,103,104,105) of prosthetic knee implants, and methods of fixating the components to one another and, especially fixation of the implants to bone.

23 Claims, 23 Drawing Sheets

(51) Int. Cl.
*A61F 2/38* (2006.01)
*A61F 2/40* (2006.01)

(56) References Cited

U.S. PATENT DOCUMENTS

| | | | |
|---|---|---|---|
| 4,950,258 | A | 8/1990 | Kawai et al. |
| 5,108,289 | A | 4/1992 | Fukuyo |
| 5,951,288 | A | 9/1999 | Sawa |
| 6,126,693 | A | 10/2000 | O'Neil et al. |
| 6,160,084 | A | 12/2000 | Langer et al. |
| 6,277,390 | B1 | 8/2001 | Schaffner |
| 6,281,262 | B1 | 8/2001 | Shikinami |
| 6,299,448 | B1 | 10/2001 | Zdrahala et al. |
| 6,875,235 | B2 * | 4/2005 | Ferree ................ 623/20.32 |
| 7,160,328 | B2 | 1/2007 | Rockwood, Jr. et al. |
| 2001/0018616 | A1 | 8/2001 | Schwab |
| 2004/0030341 | A1 | 2/2004 | Aeschlimann et al. |
| 2005/0143837 | A1 | 6/2005 | Ferree |
| 2006/0190086 | A1 | 8/2006 | Clemow et al. |
| 2006/0241759 | A1 * | 10/2006 | Trieu ................ 623/17.11 |
| 2007/0083205 | A1 | 4/2007 | Attawia et al. |
| 2009/0149856 | A1 | 6/2009 | Paakinaho et al. |

FOREIGN PATENT DOCUMENTS

| | | |
|---|---|---|
| DE | 198 29 589 A1 | 1/2000 |
| DE | 102005032005 A1 | 1/2007 |
| EP | 1 000 958 A1 | 5/2000 |
| EP | 1000958 A1 | 5/2000 |
| EP | 1 762 201 A1 | 3/2007 |
| FR | 2 378 505 | 8/1978 |
| FR | 2 784 288 A1 | 4/2000 |
| FR | 2863478 A1 | 6/2005 |
| GB | 1416575 A | 12/1975 |
| GB | 1 507 309 | 4/1978 |
| GB | 2 004 465 A | 4/1979 |
| JP | 51-64794 | 6/1976 |
| JP | 9-149909 | 6/1997 |
| JP | 09234241 A | 9/1997 |
| JP | 2000-126213 | 5/2000 |
| JP | 2001-87292 | 4/2001 |
| JP | 2001-293019 | 10/2001 |
| JP | 2008-541785 | 11/2008 |
| WO | 9622061 A1 | 7/1996 |
| WO | WO 2006/091495 A2 | 8/2006 |
| WO | WO 2007/024689 A2 | 3/2007 |
| WO | WO 2007/101267 A1 | 9/2007 |
| WO | 2008131197 A1 | 10/2008 |

OTHER PUBLICATIONS

English Computer Translation for JP 09-234241 "Orthosis Having Thermally Deforming Property" Shimadzu Corp., 1 page.
Nulend, et al., "Increased Calcification of Growth Plate Cartilage as a Result of Compressive Force in Vitro," Arthritis & Rheumatism, 29(8):1002-1009(1986), 13 pages.
Nulend, et al., "Inhibition of Osteoclastic Bone Resorption by Mechanical Stimulation in Vitro," Arthritis & Rheumatism, 33(1):66-72 (1999), 11 pages.
International Preliminary Report on Patentability mailed Oct. 20, 2009, which was received in corresponding application No. PCT/US2008/060821, 9 pages.
English Patent Abstract of DE 102005032005 from esp@cenet, Publication Date Jan. 11, 2007.
Shen, et al., "Irradiation of Chemically Crosslinked Ultrahigh Molecular Weight Polyethylene," Journal of Polymer Science: Part B: Polymer Physics, vol. 34, 1063-1077 (1996), 15 pages.
Narkis, et al., "Some Properties of Silane-Grafted Moisture-Crosslinked Polyethylene," Polymer Engineering and Science, Sep. 1985, vol. 25, No. 13, 6 pages.
Gugumus, "Possibilities and limits of synergism with light stabilizers in polyolefins 2. UV absorbers in polyolefins," Polymer Degradation and Stability 75 (2002) 309-320, 12 pages.
Costa, et al., "Mechanisms of Crosslinking, Oxidative Degradation and Stabilization of UHMWPE," UHMWPE Biomaterials Handbook, Chapter 21, Copyright 2009, 15 pages.
Al-Malaika, et al., "Processing Effects on Antioxidant Transformation and Solutions to the Problem of Antioxidant Migration," Advances in Chemistry, American Chemical Society: Washington, DC, May 5, 1996, 15 pages.
English Patent Abstract of FR 2863478 from esp@cenet, published Jun. 17, 2005, 1 page.
International Search Report, International Application No. PCT/US2008/060406, 6 pages.
Chinese Search Report; Chinese Patent Application No. 200880021062.3; Mar. 7, 2013; 4 pages.
Chinese First Office Action; Chinese Patent Application No. 200880021062.3; Mar. 27, 2013; 18 pages.
Notice of Reasons for Rejection, Japanese Patent Application No. 2010-504202, 5 pages.
First Examination Report; European Patent Office; European Patent Application No. 08 745 914.5; Mar. 21, 2014; 7 pages.
Patent Examination Report No. 2; Australian Patent Office; Australian Patent Application No. 2008243037; 3 pages.
Chinese Second Office Action; Chinese Patent Application No. 200880021062.3; Feb. 12, 2014; 7 pages.
First Office Action; Canadian Intellectual Property Office; Canadian Patent Application No. 2,686,119; Mar. 27, 2014; 3 pages.

* cited by examiner

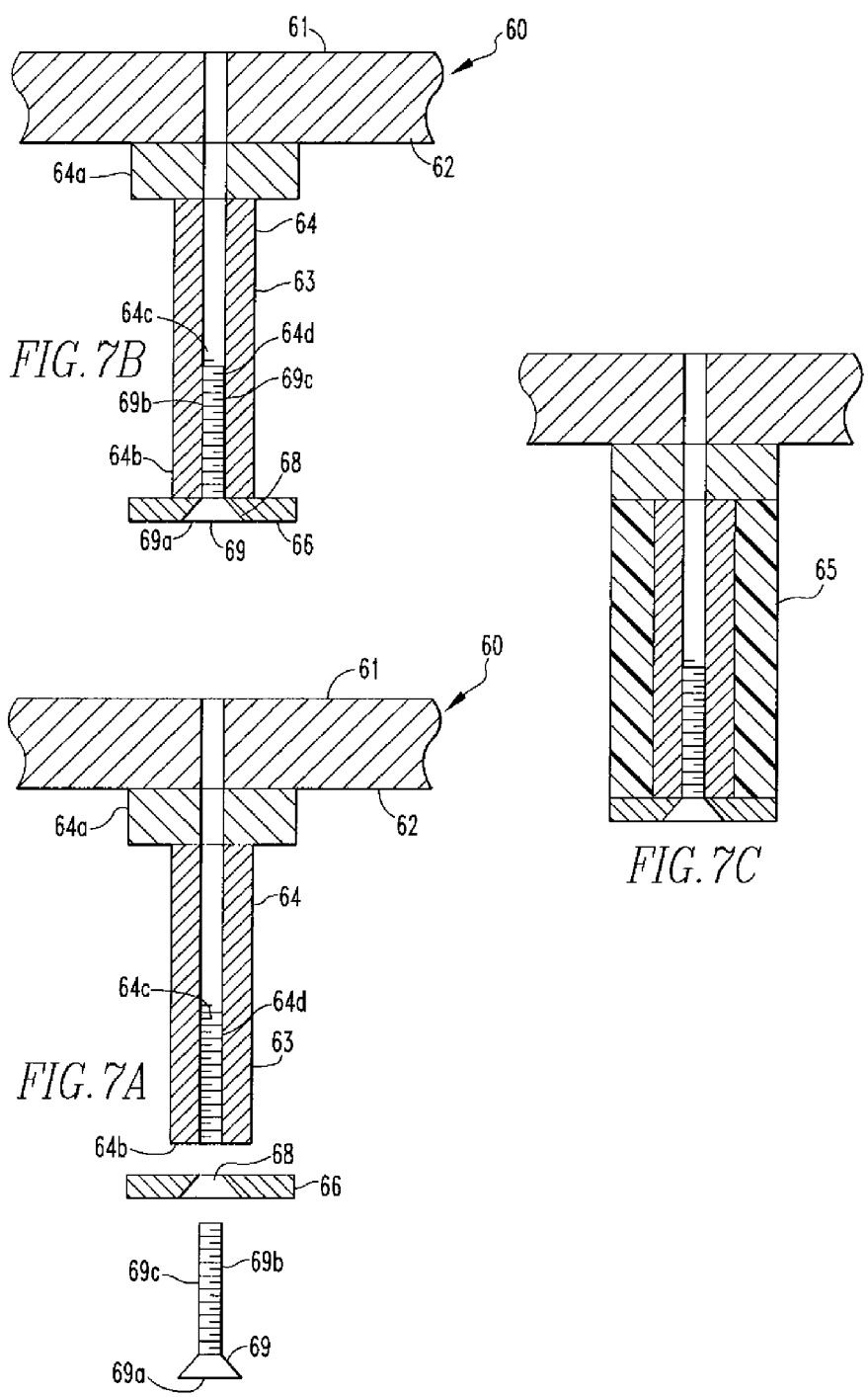

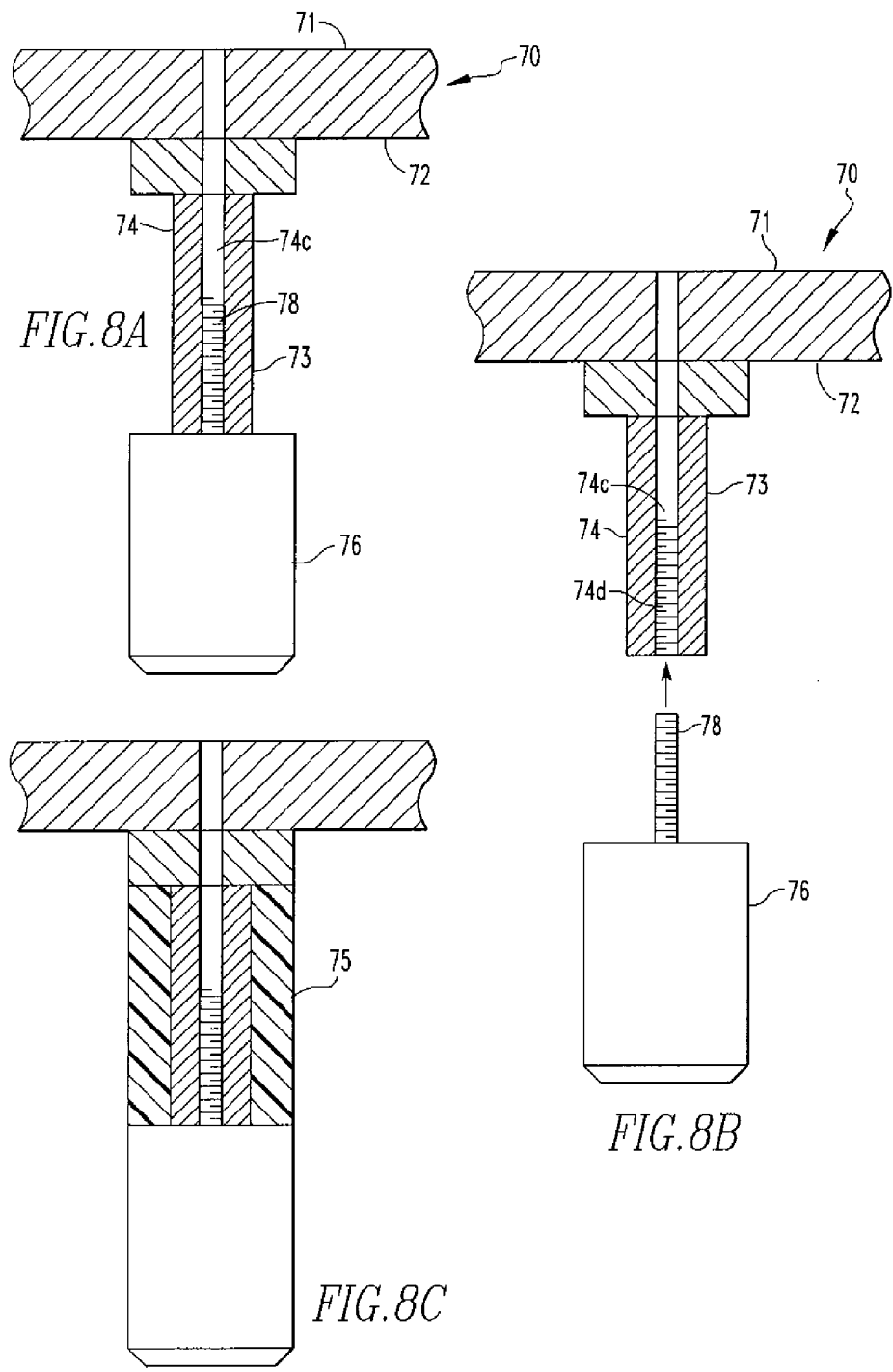

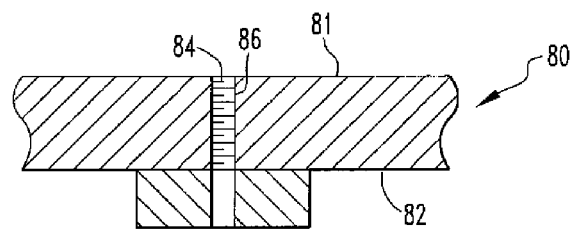
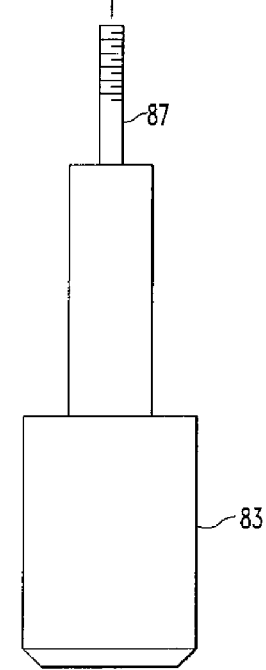
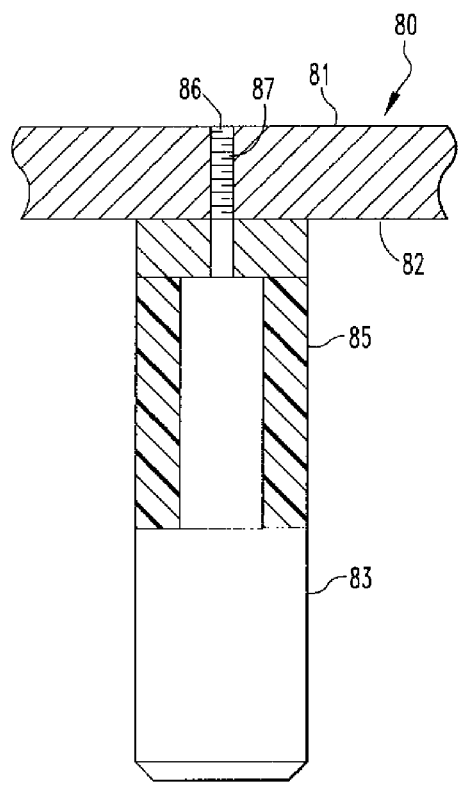
FIG.9A
FIG.9B

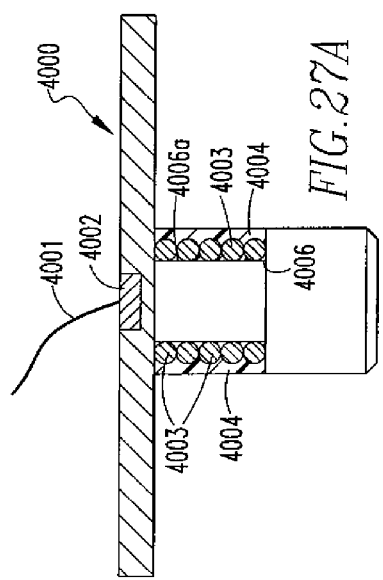
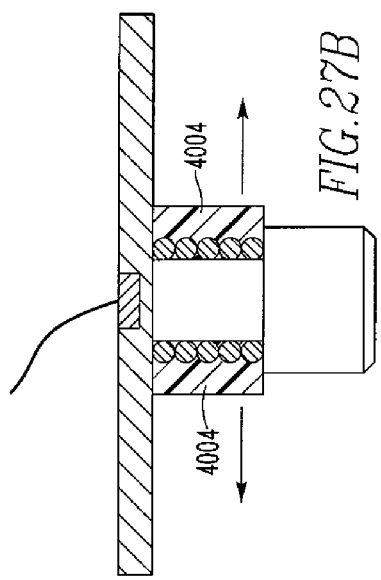
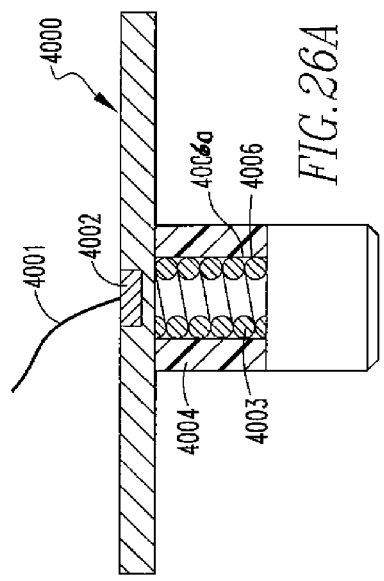
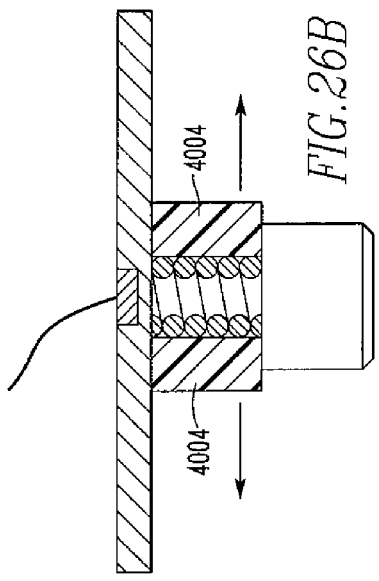

KNEE AND SHOULDER JOINT PROSTHESIS

CROSS-REFERENCE TO RELATED APPlICATIONS

This application is a United States National Phase filing of International Application No. PCT/US2008/060406 which claims priority to U.S. Patent Application No. 60/988,640 filed on Nov. 16, 2007, U.S. Patent Application No. 60/912,693 filed on Apr. 19, 2007, and United States Patent Application No. 60/912,740 filed on Apr. 19, 2007, the disclosures of which are incorporated herein by reference in their entirety.

BACKGROUND OF THE INVENTION

1. Field of the Invention

The present disclosure relates to prosthetic implants and more specifically, prosthetic implants that include polymer material for fixation of the implant to bone and fixation between component parts.

2. Related Art

Often within orthopaedic devices, implants contain stems, fins, and screws which act as anchoring devices upon implantation. Initial and long lasting fixation is commonly obtained via bone cement or porous in-growth fixation surfaces. When the latter option is utilized, initial fixation is key in the long term survivorship of the implanted device. Often press fit sterns, and screw fixations provide the means in which these devices are held in position until bone in-growth occurs. These frequently create stress patterns in the bone and produce undesirable bone remodeling that can lead to destabilization of the implant. In addition, these devices remain after the implant is well fixed.

SUMMARY OF THE INVENTION

In one aspect, the present disclosure relates to a tibial tray for a knee prosthesis. The tray includes at least one fixator for holding the tray on a patient's proximal tibia and a polymer material coupled to the fixator. In an embodiment, the tray includes multiple fixators. In another embodiment, the fixator includes an interface portion, such as a shaped interface portion, and a polymer material coupled to the interface portion. In yet another embodiment, the fixator includes an upper portion and a lower portion being releasably coupled to each other, wherein the polymer material is located between the upper portion and the lower portion. In a further embodiment, the fixator is releasably coupled to a distal surface of the tibial tray. In yet a further embodiment, the polymer material includes more than one part. In yet an even further embodiment, the tray further includes a post located on a proximal surface of the tibial tray, wherein the post extends perpendicular to the proximal surface and includes a polymer material. The polymer material includes shape memory qualities and is selected from a group that includes an amorphous polymer, a semi-crystalline polymer, and combinations thereof.

In another aspect, the present disclosure relates to a femoral component for a knee prosthesis. The femoral component includes at least one femoral condyle, at least one peg for holding the femoral component on a patient's distal femur, and a polymer material coupled to the peg. The peg is located on a proximal surface of the femoral condyle. The polymer material includes shape memory qualities and is selected from a group that includes an amorphous polymer, a semi-crystalline polymer, and combinations thereof.

In yet another aspect, the present disclosure relates to a knee prosthesis that includes a tibial tray having at least one fixator for holding the tray on a patient's proximal tibia and a post located on a proximal surface of the tibial tray, a polymer material coupled to the fixator and the post, a femoral component including at least one femoral condyle having at least one peg for holding the femoral component on a patient's distal femur, a polymer material coupled to the peg, and a tibial insert having a proximal surface that is shaped to engage the femoral component, wherein the tibial insert has a distal surface that fits against and articulates with the proximal surface of the tibial tray. The fixator is located on a distal surface of the tray and the post extends perpendicular to the proximal surface of the tray. The peg is located on a proximal surface of the femoral condyle. In an embodiment, the tibial insert includes a channel extending therethrough, wherein the post of the tibial tray extends through the channel. In another embodiment, the channel includes a polymer material.

In a further aspect, the present disclosure relates to a knee prosthesis that includes a tibial tray having at least one fixator for holding the tray on a patient's proximal tibia and a first locking mechanism located on a proximal surface of the tray, a polymer material coupled to the fixator, a femoral component that includes at least one femoral condyle having at least one peg for holding the femoral component on a patient's distal femur, a polymer material coupled to the peg, and a tibial insert having a proximal surface that is shaped to engage the femoral component and a second locking mechanism shaped to engage the first locking mechanism and coupled the tibial insert to the tibial tray. The fixator is located on a distal surface of the tray and the peg is located on a proximal surface of a femoral condyle. The second locking mechanism is located on a distal surface of the tibial insert. In an embodiment, either the first locking mechanism or the second locking mechanism includes a polymer material. The polymer material includes shape memory qualities and is selected from a group that includes an amorphous polymer, a semi-crystalline polymer, combinations thereof, a copolymer, and a polymer blend.

In another aspect, the present disclosure relates to a shoulder prosthesis that includes a stem, a humeral component coupled to the stem, a glenoid component coupled to the humeral component, and a shape memory polymer material coupled to the glenoid component. In an embodiment, the polymer material is selected from a group that includes an amorphous polymer, a semi-crystalline polymer, and combinations thereof.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the present disclosure. In the drawings:

FIGS. 5A and 513 show a perspective view of a fourth embodiment of a tibial tray of the present disclosure.

FIGS. 7A-7C show a perspective view of a sixth embodiment of a tibial tray of the present disclosure.

FIGS. 8A-8C show a perspective view of a seventh embodiment of a tibial tray of the present disclosure.

FIGS. 9A-9B show a perspective view of an eighth embodiment of a tibial tray of the present disclosure.

FIGS. 26A-26B show perspective views of a nineteenth embodiment of a tibial tray of the present disclosure.

FIGS. 27A-27B show perspective views of a twentieth embodiment of a tibial tray of the present disclosure.

DETAILED DESCRIPTION OF THE EMBODIMENTS

The following description of the preferred embodiment(s) is merely exemplary in nature and is in no way intended to limit the present disclosure, its application, or uses.

Figure 1A:
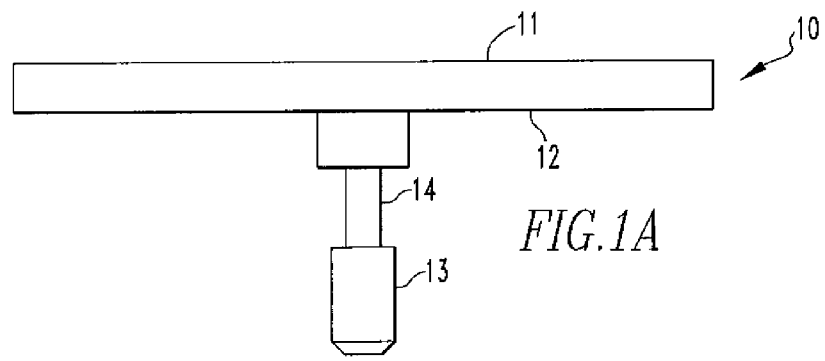
FIGS. 1A-1B show perspective views of a first embodiment of a tibial tray of the present disclosure.
Figure 1B:
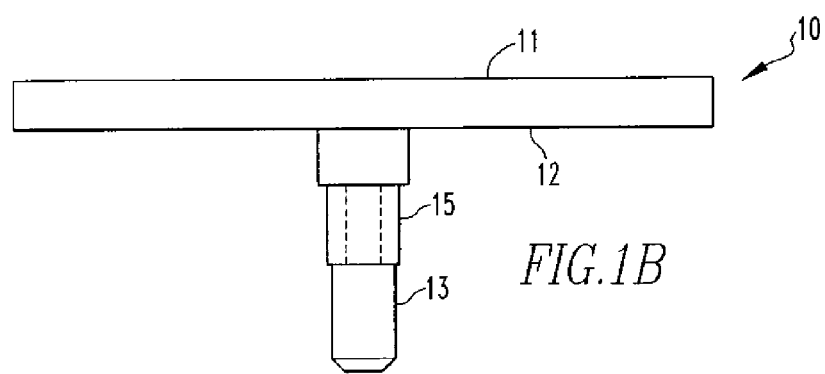
Figure 1C:
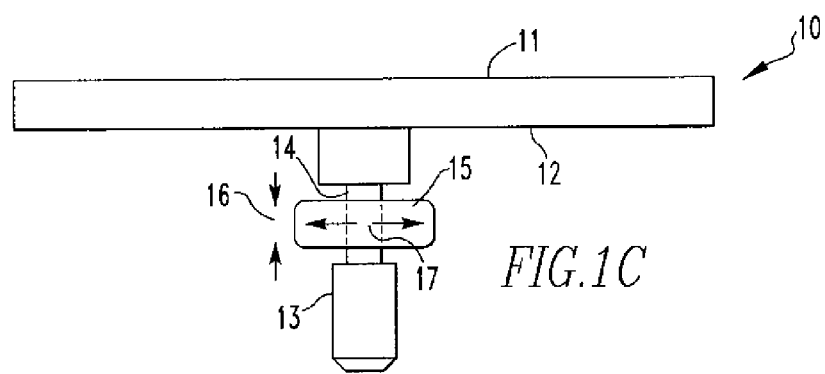
FIG. 1C shows a perspective view of the tibial tray of FIGS. 1A-1B after deformation of the polymer material.

FIGS. 1A, 1B, and 1C show a tibial tray 10 for a knee prosthesis. The tray 10 has a flat proximal surface 11 and a generally flat distal surface 12 that mates with and faces a surgically prepared proximal surface of a tibia (not shown). The tray 10 includes a fixator 13 for enhancing implantation to the patient's proximal tibia. The fixator 13 includes a shaped interface portion 14 having a polymer material 15 coupled thereto. The shaped interface portion 14 can be of any shape that allows formation of bonds between the polymer material 15 and the shaped interface portion 14 once the polymer material 15 is provided with energy, as described below. The shaped interface portion 14 may include a shape that is circular, triangular, rectangular, star-shaped, oval, or hexagonal. In addition, the surface of the shaped interface portion 14 may be tapered or beveled or include axial, radial, and/or helical grooves. These shapes and surfaces help the polymer material engage the fixator 13 to provide support for axial and torsional loading and to substantially reduce motion in those directions after the fixator 13 has been placed in a bone, as will be further described below. The shapes and surfaces can be machined, molded, cast, laser cut, or chemically etched into the internal fixation device or formed via another method known to one of ordinary skill in the art. Machining of the shapes and surfaces could take many forms, including wire and ram electrical discharge machining (EDM). In addition, the shaped interface portion may be located anywhere along the fixator.

Multiple shaped interface portions, each including a polymer material, may be present on the fixator and the portions may include a surface and a shape having a cross-section as described above. The shaped interface portions may be present anywhere along the fixator. Furthermore, the tray may include multiple fixators to further enhance implantation to the proximal tibia. The fixators may be of the same shape and size as the fixator in FIGS. 1A-1C or may be of different shapes and sizes.

The polymer material that is coupled to the shaped interface portion includes an orientated resorbable or non-resorbable material and is selected from a group that includes an amorphous polymer, a semi-crystalline polymer, or a composition having a combination thereof. Factors used to determine the type of polymer used on the shaped interface portion, include, but are not limited to, the desired amount of polymer deformation, the desired rate at which that deformation occurs, the rate at which the polymer is absorbed, the strength of the polymer, and the transition temperature of the polymer.

The polymer material is processed, via a process such as die drawing, extrusion, or other process known to one of skill in the art, to have shape memory qualities and, as shown in FIG. 1C, changes shape or deforms by shrinking axially 16, or along the length of the material, and expanding radially 17, or along the width of the material. Although, in certain instances, it is possible for the material to shrink radially and expand axially or expand or shrink in one direction and not expand or shrink in another direction. This expansion and shrinkage causes an interference fit between the polymer material and the bone, thereby fixating the tibial tray to the bone.

Generally, polymers that display shape memory qualities show a large change in modulus of elasticity at the glass transition temperature ($T_g$). The shape-memory function can be achieved by taking advantage of this characteristic. Namely, a molded article (primary molded article) to which a definite shape (the original shape) has been imparted by a common method for molding plastics is softened by providing the article with energy and heating to a temperature ($T_f$)

higher than the $T_g$ of the polymer, but lower than the melting temperature ($T_m$) thereof so as to deform it into a different shape. Next, the molded article is cooled to a temperature lower than the $T_g$, while maintaining the thus deformed shape (secondary molded article). When it is heated again to a temperature higher than the secondary molding temperature $T_f$, but lower than the $T_m$, the shape of the secondary molded article disappears and thus the article is recovered to the original shape of the primary molded article.

For the purposes of this disclosure, a molded article having a definite shape (original shape) is formed from polymer material and is provided with energy to heat the article to a temperature above the glass transition temperature of the polymer, but lower than the melting temperature ($T_m$) thereof so as to deform it into a different shape and effectively wedge the article between two components, which in this case, is the fixator and the bone. In this manner, the tibial tray becomes fixed to the bone. However, rather than cooling the article and heating it again until it recovers its original shape, the article is kept in this deformed shape so as to maintain fixation of the tray to the bone. The glass transition temperature of the polymer material will vary based on a variety of factors, such as molecular weight, composition, structure of the polymer, and other factors known to one of ordinary skill in the art.

Examples of adding energy to heat the shape memory polymer material include electrical and/or thermal energy sources. It is also within the scope of this disclosure that once the component is placed in the bone, body heat would be transferred from blood and tissue, via thermal conduction, to provide the energy necessary to deform the shape memory polymer material. In this instance, body temperature would be used as the thermal energy source. Furthermore, the shape memory polymer material could be deformed via other methods known to those of ordinary skill in the art, including, but not limited to, the use of force, or mechanical energy, a solvent, a magnetic field, infrared technology, microwaves, hot gases, and/or ethylene oxide (EtOx). Any suitable force that can be applied either preoperatively or intra-operatively can be used. One example includes the use of ultrasonic devices, which can deform the polymer material with minimal heat generation. Solvents that could be used include organic-based solvents and aqueous-based solvents, including body fluids. Care should be taken that the selected solvent is not contra indicated for the patient, particularly when the solvent is used intra-operatively. The choice of solvents will also be selected based upon the material to be deformed. Examples of solvents that can be used to deform the shape memory polymer material include alcohols, glycols, glycol ethers, oils, fatty acids, acetates, acetylenes, ketones, aromatic hydrocarbon solvents, and chlorinated solvents. Finally, the shape memory polymer material could include magnetic particles and deformation could be initiated by inductive heating of the magnetic particles through the use of a magnetic field.

Specific polymers that may be used for the shaped interface portion and/or the device include polyetheretherketone (PEEK), polymethyl methacrylate (PMMA), polyethyl methacrylate (PEMA), polyacrylate, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof.

In addition, bioactive agents may be incorporated into the polymer material to be released during the deformation or the degradation of the polymer material. These agents are included to help promote bone regrowth. Examples include bone morphogenic proteins, antibiotics, anti-inflamatories, angiogenic factors, osteogenic factors, monobutyrin, omental extracts, thrombin, modified proteins, platelet rich plasma/solution, platelet poor plasma/solution, bone marrow aspirate, and any cells sourced from flora or fawna, such as living cells, preserved cells, dormant cells, and dead cells. Other bioactive agents known to one of ordinary skill in the art may also be used.

Furthermore, the polymeric materials can be formed as a composite or matrix and include reinforcing material or phases such as fibers, rods, platelets, and fillers. For example, the polymeric material can include glass fibers, carbon fibers, polymeric fibers, ceramic fibers, or ceramic particulates. Other reinforcing material or phases known to one of ordinary skill in the art could also be used.

The polymer material, as described above, may include a porogen, such as sodium chloride. The porogen may then be washed out of the material leaving pores that will aid water penetration and hence accelerate the relaxation rate of the material. Porogens may be included in the material and washed out to leave pores before the material is oriented. Upon orientation of the material, channels will develop in the material, due to an increase in surface area, to aid in water penetration and relaxation rate. The addition of these channels, pores, porogens, and hydrophilic units enhances the rate of relaxation of these materials. Alternatively, the porogens may be included in the device, such that upon placing the device in the body, the porogens dissolve out of the device, thereby leaving pores in the device. The effect of porogens, such as sodium chloride (NaCl), on the relaxation rate of the material. The effect of these porogens on the relaxation rate of the material may be varied by having a mixture of porogens with a range of solubilities and sizes. Other methods of varying the effect of these porogens, known to one of skill in the art, may also be used.

Figure 2:
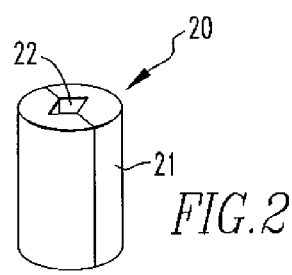
FIG. 2 shows a perspective view of a sleeve of polymer material for use on a fixator of a tibial tray of the present disclosure.

The polymer material could include a sleeve of material having a uniform structure with an outside surface and a channel running through the middle of the structure with both the structure and the channel having the same or different shapes. As shown in FIG. 2, the polymer material is in the form of a sleeve 20 having a cylindrical structure with an outside surface 21 that is circular and a channel 22 having a shape to match the shape of the interface portion. However, the structure of the sleeve 20 and the channel 22 may have another shape. The sleeve 20 is shown as having two parts, but may be of a one-part construction. The sleeve 20 may be formed by die-drawing or molding (i.e. compression flow molding or thermoforming process) the above-mentioned polymers or polymer compositions. The channel 22 may be formed in the sleeve 20 during the die drawing or molding process. Alternatively, the channel 22 may be formed in the sleeve 20, post processing by drilling, or by any other method of forming the channel 22.

In addition, the polymer material may not be in the form of sleeve, but rather there may be several strips of polymer material each of which have a structure and each of which are coupled to the shaped interface portion or within the grooves or other possible features on the surface of the shaped interface portion, as described above. The strips may be formed by the processes listed above or by another process, such as an extrusion process (i.e. single screw, twin screw, disk, ram, or pulltrusion process).

The tibial tray may be manufactured from a metal, such as titanium, titanium alloys, steel, stainless steel, cobalt-chromium alloys, tantalum, magnesium, niobium, nickel, nitinol, platinum, silver, and combinations thereof Other metals known to one of ordinary skill in the art could also be used.

The fixator may be manufactured from a metal, non-metal, or a resorbable or non-resorbable polymer material, which may be the same polymer material used on the shaped interface portion, as described above, or another type of polymer material.

FIGS. 3A-3C, 4A-4C, 5A-5B, and 6A-6B show further examples of a tibial tray that includes a fixator and a polymer material coupled to the fixator. The fixators in these figures do not include a shaped or recessed interface portion, but rather have outer diameters that are uniform throughout the length of the fixator.

Figure 3A:
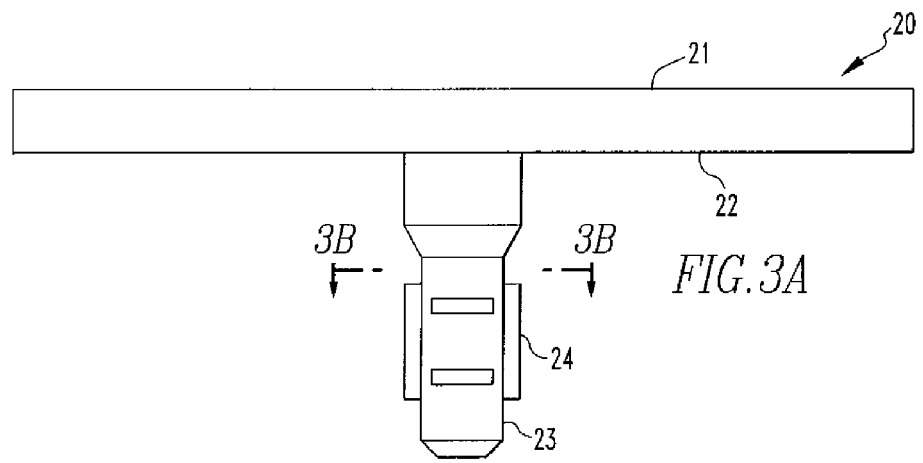
FIGS. 3A and 3C show a perspective view of a second embodiment of a tibial tray of the present disclosure.
Figure 3B:
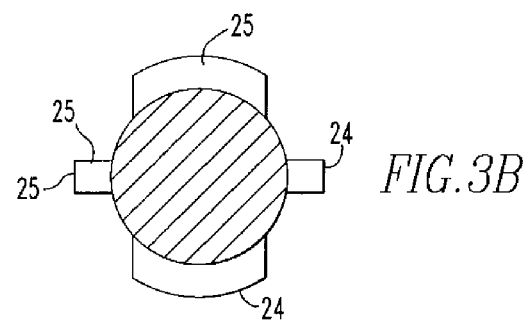
FIG. 3B shows a top view of the fixator of the tibial tray of FIGS. 3A and 3C.
Figure 3C:
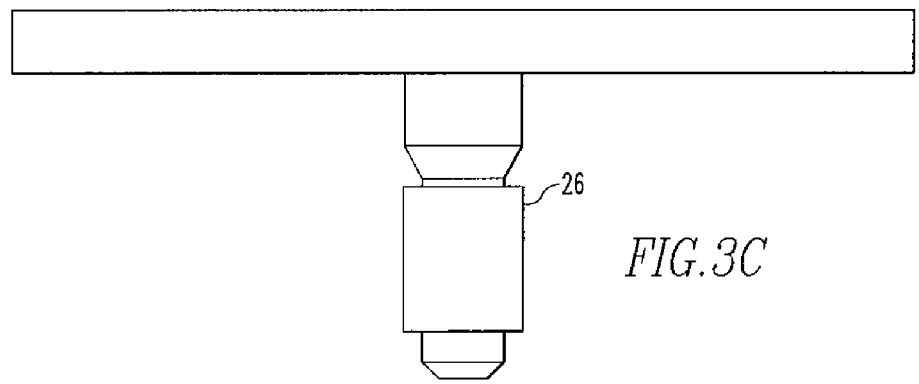

As shown in FIGS. 3A-3C, the fixator 23 includes protrusions 24 on a surface of the fixator 23. The protrusions 24 may be coupled to the surface via a variety of methods. For example, the fixator 23 may include slotted regions that at least a portion of the protrusion 24 would be placed in to create an interference fit between the fixator 23 and the protrusion 24. In addition, the protrusion 24 may be coupled to the surface of the fixator 23 by soldering or welding or through the use of an adhesive. Any other method known to one of ordinary skill in the art may also be used to couple the protrusion 24 to the fixator 23. In addition, the number and location of the protrusions 24 on the fixator 23 may vary. Furthermore, as shown in FIG. 3B, the protrusions 24 may be either perpendicular or parallel to a longitudinal axis of the fixator 23. However, the protrusions 24 may be placed at other locations relative to the longitudinal axis of the fixator 23 also. Surfaces 25 of the protrusions 24 may include features that would further allow formation of bonds between the polymer material 26 and the protrusions 24 and engagement of the fixator 23 to provide support for axial and torsional loading and to substantially reduce motion in those directions after the fixator 23 has been placed in a bone. As shown in FIG. 3C the polymer material 26 is in the form of a sleeve that covers the interface portion. However, the material is not limited to a sleeve, but rather may be strips of polymer material located either on the fixator 23 or the protrusions 24. Furthermore, it is within the scope of this disclosure, that the protrusions 24 may be made solely out of a polymer material having shape memory qualities.

Figure 4A:
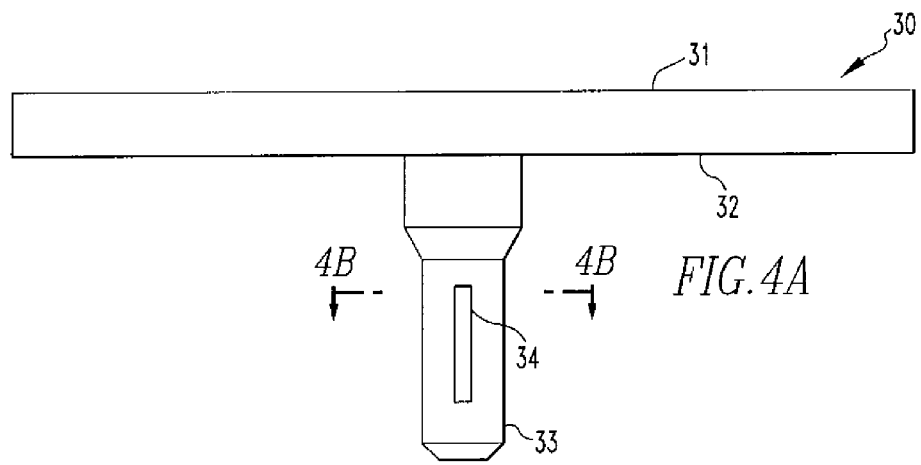
FIGS. 4A and 4C show a perspective view of a third embodiment of a tibial tray of the present disclosure.
Figure 4B:
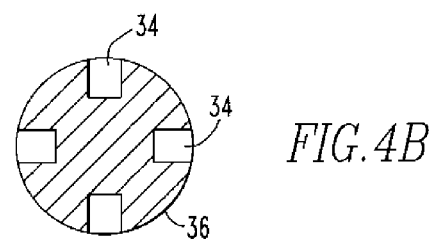
FIG. 4B shows a top view of the fixator of the tibial tray of FIGS. 4A and 4C.
Figure 4C:
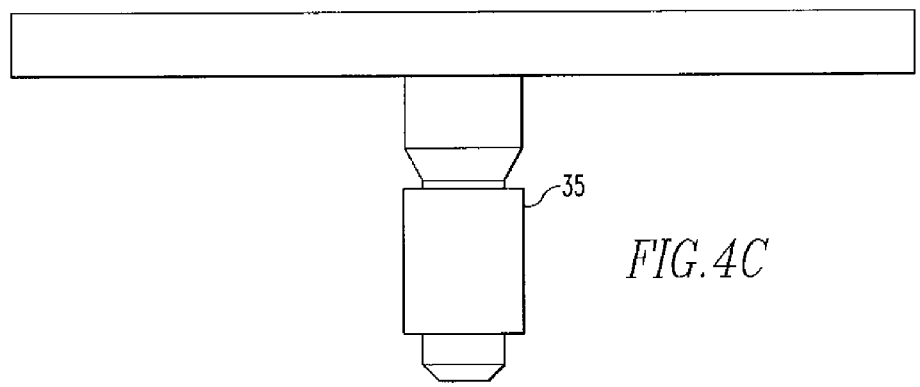
Figure 5A:
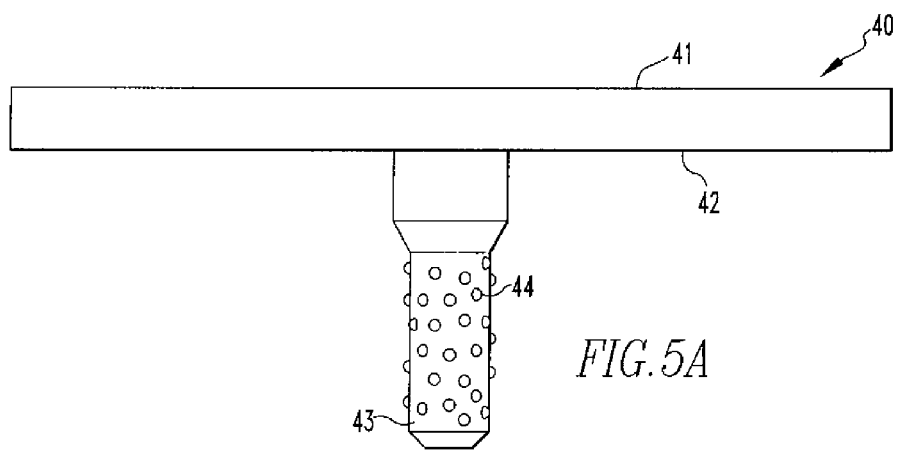
Figure 5B:
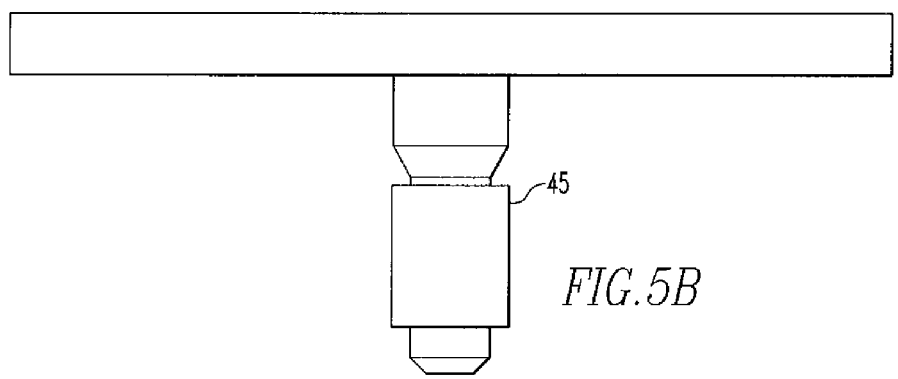
Figure 6A:
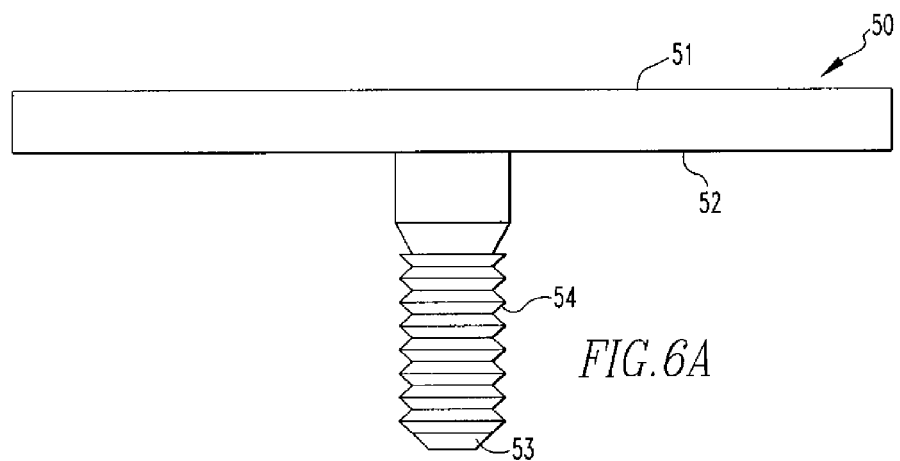
FIGS. 6A and 6B show a perspective view of a fifth embodiment of a tibial tray of the present disclosure.
Figure 6B:
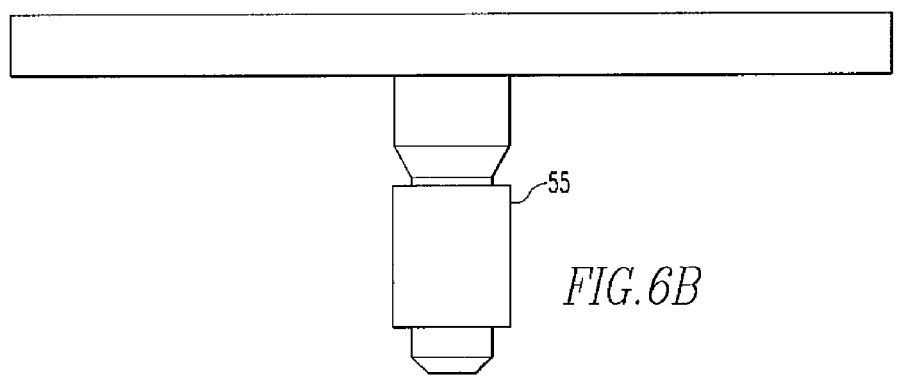

FIGS. 4A-4B show a tibial tray fixator 33 that includes slots 34 that extend inward from an outer surface 36 of the fixator 33. The number, size, and location of the slots 34 may vary. In addition, the slots 34 may be parallel with a longitudinal axis of the fixator 33 or they may be placed at another location relative to the fixator 33. As shown in FIG. 4C, a polymer material 35 is coupled to the fixator 33. When the polymer material 35 is provided with energy, the material 35 deforms and not only expands outwardly to engage the bone, but also expands inwardly to engage the slots 34 and provide the tray 30 with support for axial and torsional loading and reduced motion in those directions.

FIGS. 5A-5B and 6A-6B show a tibial tray 40,50 that includes a fixator 43,53 having a porous beaded or roughened outer surface 44 and a threaded outer surface 54, respectively, and a polymer material 45,55 coupled to the fixator 43,53. The outer surface features 44,54 enhance the formation of bonds between the polymer material 45,55 and the fixator 43,53 once the polymer material 45,55 is provided with energy and provide the tray 40, 50 with support for axial and torsional loading and reduced motion in those directions. In addition, the porous outer surface 44 allows for the in-growth of bone as the material 45 is resorbed into the body. Furthermore, for the purposes of FIGS. 5A-5B and 6A-6B, the entire fixator 43,53 includes the surface features 44,54 shown. However, it is within the scope of this disclosure that the fixator 43,53 could be partially covered with the surface features 44,54 or that the surface features 44,54 could be located in multiple areas along the length of the fixator 43,53. Also, surface features other than those shown and that would promote firm fixation of the material to the fixators 43,53 after the material 44,55 was provided with energy, could also be used.

FIGS. 7A and 7B shows a tibial tray 60 that includes a fixator 63 having an upper portion 64 and a lower portion 66, wherein the upper portion 64 and the lower portion 66 are releasably coupled to each other. The upper portion 64 includes a proximal end 64a, a distal end 64b, and a channel 64c, which extends the length of the upper portion 64, and includes a threaded inner wall 64d. The lower portion 66, which includes an opening 68 that extends therethrough, is coupled to the upper portion 64 by placing the lower portion 66 at the distal end 64b of the upper portion 64, such that the opening 68 is aligned with the channel 64c, and a fastener 69 is then inserted through the opening 68 and into the channel 64c to couple the lower portion 66 to the upper portion 64. The fastener 69 includes a head 69a and an outer surface 69b that has threads 69c to match the threaded inner wall 64d of the channel 64c and allow for axially oriented advancement of the fastener 69 into the channel 64c. As shown in FIG. 7C, polymer material 65 is located between the upper and lower portions 64,66. The polymer material 65 may be in the form of a one-piece or multiple-piece sleeve, as described above. The fixator 63 may include a shape or surface feature that would enhance fixation of the polymer material 65 to the fixator 63 after deformation of the material 65. In addition, for the purposes of FIGS. 7A-7C, the fastener 69 is a screw, but could include a rod, pin, or any other fastener that would couple the lower portion 66 to the upper portion 64.

Similar to FIGS. 7A-7C, FIGS. 8A-8C show a tibial tray 70 that includes a fixator 73 having an upper portion 74 and a lower portion 76, wherein the upper portion 74 and the lower portion 76 are releasably coupled to each other. However, the lower portion 76 includes a threaded stem portion 78 that mates with the threaded inner wall 74d of the channel 74c, allowing for axially oriented advancement of the threaded stem 78 into the channel 74c, and coupling of the lower portion 76 and the upper portion 74. As shown in FIG. 8C, polymer material 75 is located between the upper and lower portions 74,76. The polymer material 75 may be in the form of a one-piece or multiple-piece sleeve, as described above. The fixator 73 may include a shape or surface feature that would enhance fixation of the polymer material 75 to the fixator 73 after deformation of the material 75.

FIGS. 9A-9B show a tibial tray 80 having a proximal surface 81 and a distal surface 82, wherein the tray 80 includes a fixator 83 that is releasably coupled to the distal surface 82. The tray 80 includes a channel 84 having a threaded inner wall 86 and the fixator includes a threaded stem portion 87 that mates with the threaded inner wall 86 of the channel 84, allowing for axially oriented advancement of the threaded stem 87 into the channel 84, and coupling of the fixator 83 to the distal surface 82 of the tray 80. As shown in FIG. 9B, polymer material 85 is coupled to the fixator 83. The polymer material 85 may be in the form of a one-piece or multiple-piece sleeve, as described above. The fixator 83 may include a shape or surface feature that would enhance fixation of the polymer material 85 to the fixator 83 after deformation of the material 85.

Figure 10:
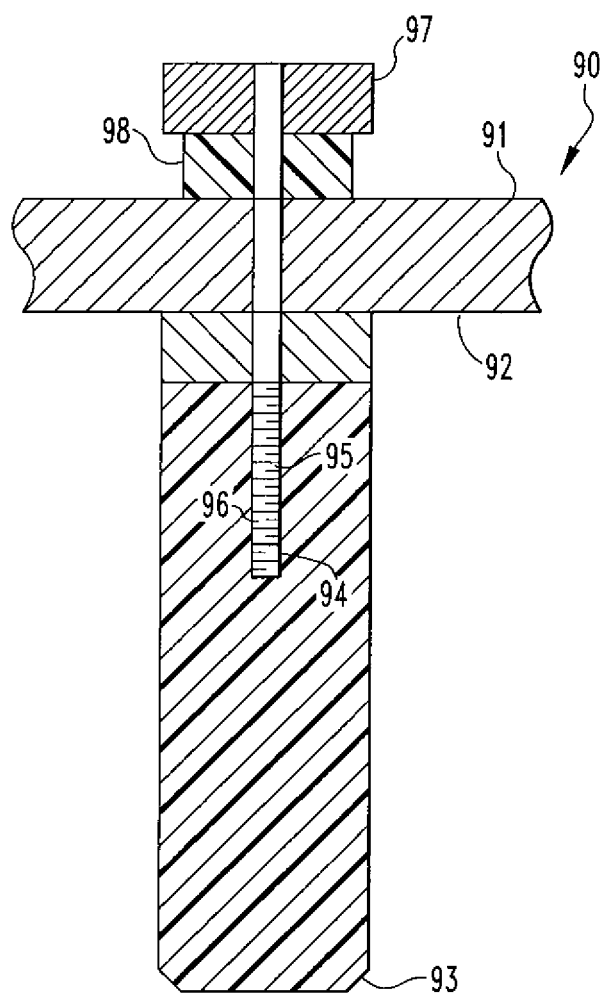
FIG. 10 shows a perspective view of a ninth embodiment of a tibial tray of the present disclosure.

FIG. 10 also shows a tibial tray 90 having a proximal surface 91 and a distal surface 92, wherein the tray 90 includes a fixator 93 that is releasably coupled to the distal surface 92. The fixator 93, which includes a polymer material, has a channel 94 that includes a threaded inner wall 95 that mates with a threaded stem portion 96, located on the distal portion 92 of the tray 90, to allow for axially oriented advancement of the threaded stem 96 into the channel 94, and coupling of the fixator 93 to the distal surface 92 of the tray 90. The polymer material of the fixator 93 is a non-resorbable shape memory polymer material. The proximal surface 91 of the tray 90 may include a post 97 that extends perpendicular to the proximal surface 91. A resorbable, shape memory polymer material 98 is coupled to the post 97. As further described below, the post 97 is used for coupling of a tibial insert (not shown) to the tibial tray 90. Once the tibial insert is coupled to the post 97, the polymer material 98 is provided with energy to deform the material 98 and fixate the insert to the post 97.

Figure 11:
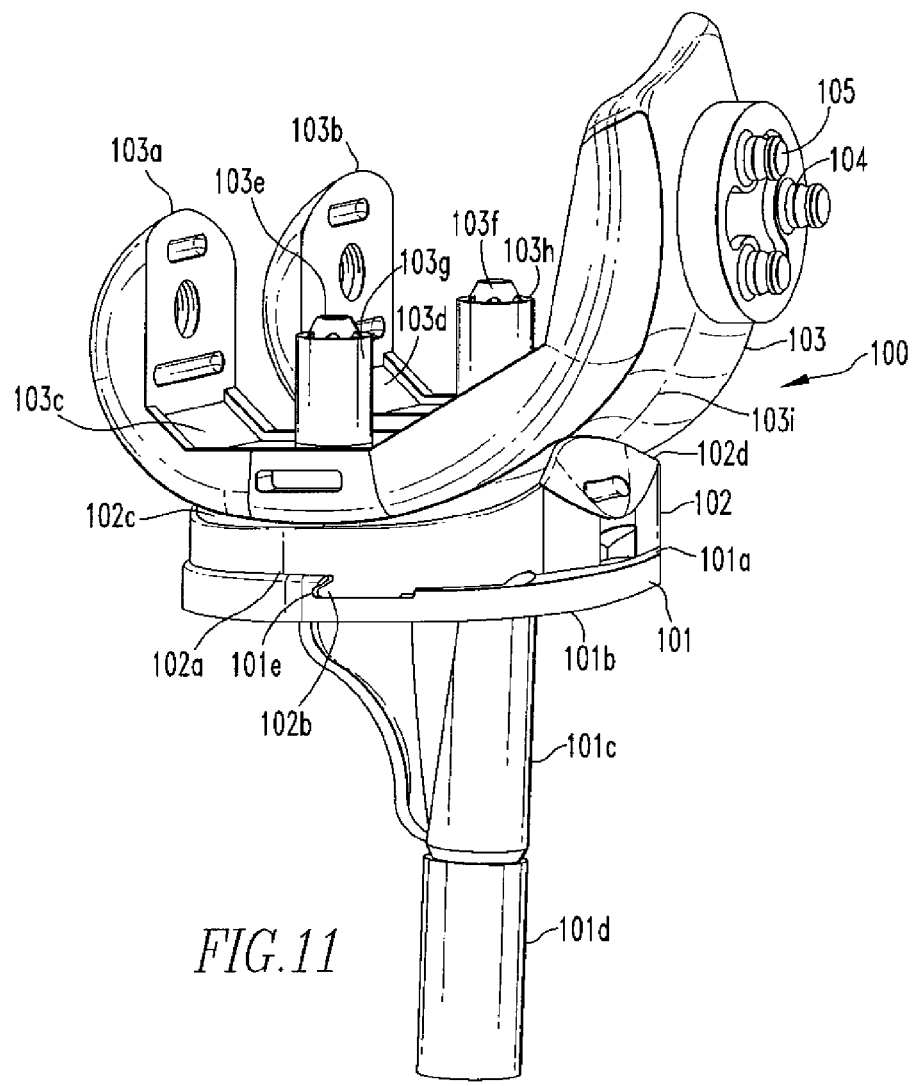
FIG. 11 shows a perspective view of a knee prosthesis of the present disclosure.
Figure 12:
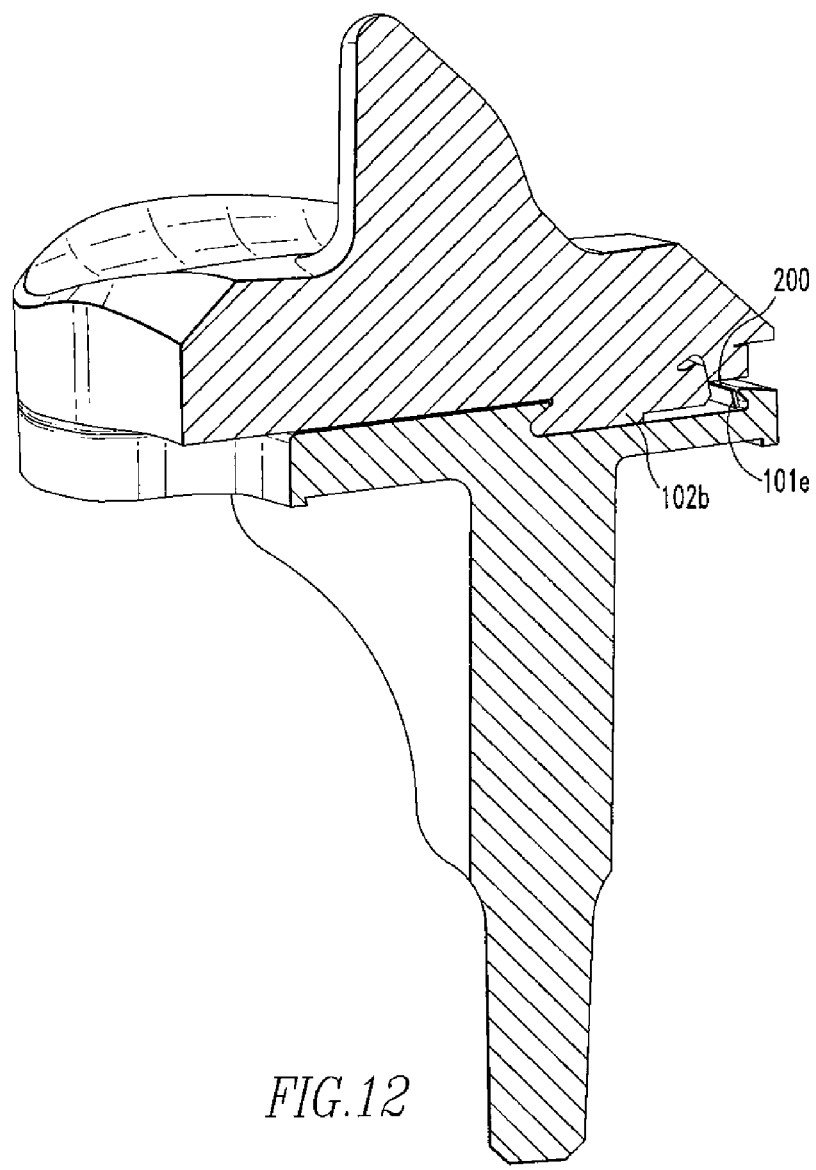
FIG. 12 shows a cross-sectional view of the first and second locking mechanisms of the tibial tray and tibial insert.

FIG. 11 shows a prosthetic knee 100 that includes a tibial tray 101, a tibial insert 102, and a femoral component 103. The tibial tray 101 includes a proximal surface 101a and a distal surface 101b. The distal surface 101b includes a fixator 101c, wherein a polymer material 101d, having shape memory qualities, is coupled to the fixator 101c. As stated above, the fixator 101c is inserted into the proximal portion of a tibial bone and the polymer material 101d is then provided with energy to deform the material 101d and fixate the tray 101 to the bone. A polymer material, having shape memory qualities, may also be coupled to the distal surface 101b such that upon providing the polymer material with energy, the material expands to engage the bone and further fixate the tray 101 to the bone. The tray 101 also includes a first locking mechanism 101e, as will be further described below. Located on the proximal portion 101a of the tray 101 is a tibial insert 102. The insert 102 provides a distal surface 102a having a second locking mechanism 102b that is shaped to engage the first locking mechanism 101e and couple the tibial insert 102 to the tibial tray 101. A pair of spaced apart concavities 102c,102d are provided for defining articulation surfaces that cooperate with correspondingly shaped articulating surfaces on a patient's femur or femoral implant. As shown in FIG. 12, the first locking mechanism 101e and/or the second locking mechanism 102b may include a shape memory polymer material 200. The material 200 is provided with energy to deform the material 200 and further fixate the insert 102 to the tray 101. Rather than having the locking mechanisms 101e, 102b, the tray 101 may include a post, such as the one shown in FIG. 10, and the tibial insert 102 may include a channel (not shown) that the post could extend through for coupling of the tray 101 and the insert 102. The insert 102 would be further fixated to the tray 101 by deformation of the polymer located on the post, as described above, or a polymer material located on an inner wall of the channel.

A femoral component 103 includes medial and lateral condylar surfaces 103a, 103b that cooperate with the spaced apart concavities 102c,102d on the tibial insert to allow for articulation of the knee joint. The proximal or interior surfaces 103c,103d of the medial and lateral condyles 103a,103b include pegs 103e,103f to facilitate fixing of the femoral component 103 to the end of a femur bone. Polymer material 103g,103h is coupled to each of the pegs 103e,103f, such that once the pegs 103e,103f are inserted into the femur bone, the polymer material 103g,103h is provided with energy to deform the material 103g,103h and further fixate the femoral component 103 to the bone. The polymer material 103g,103h may be in the form of a one-piece or multiple-piece sleeve or strips, as described above. The pegs 103e,103f may include a shape or surface feature that would enhance fixation of the polymer material 103g,103h to the pegs 103e,103f after deformation of the material 103g,103h and provide the femoral component 103 with support for axial and torsional loading and reduced motion in those directions. Defined between and parallel to the medial and lateral condyles 103a,103b is the patella groove 103i. A patella button 104 is located on a surface of the patella groove 103i. The button 104 includes extensions 105 that are inserted into the patella groove 103i to fixate the patella button 104 to the femoral component 103. A polymer material (not shown) is coupled to the outer surface (not shown) of the extensions 105 and, once the extensions 105 are inserted into the femoral component 103, the polymer material is deformed to fixate the button 104 to the component 103.

Figure 13:
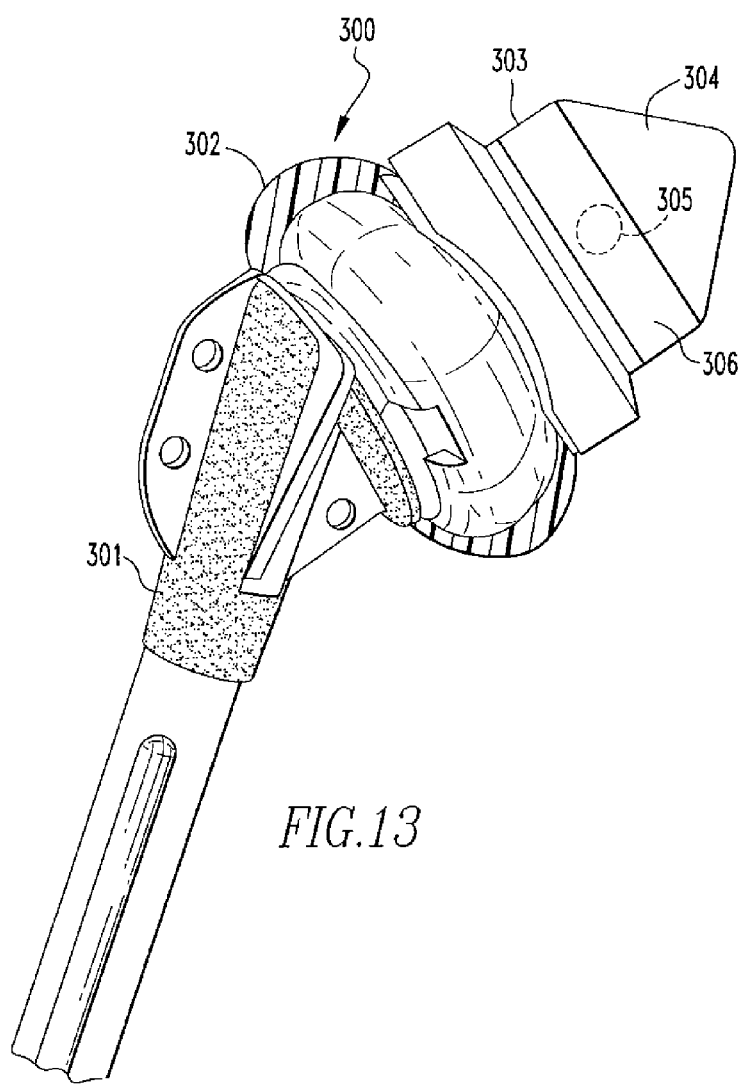
FIG. 13 shows a perspective view of a shoulder prosthesis of the present disclosure.
Figure 14A:
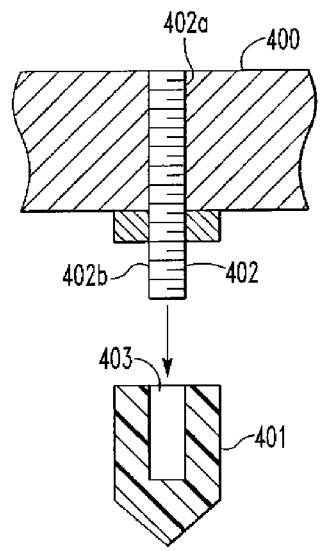
FIGS. 14A-D show a perspective view of a tenth embodiment of a tibial tray of the present disclosure.
Figure 14B:
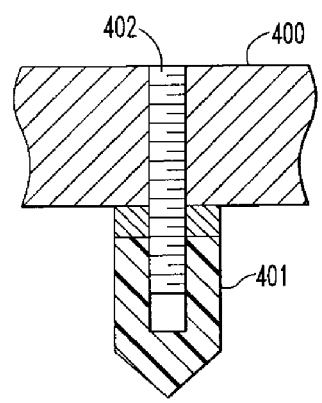
Figure 14C:
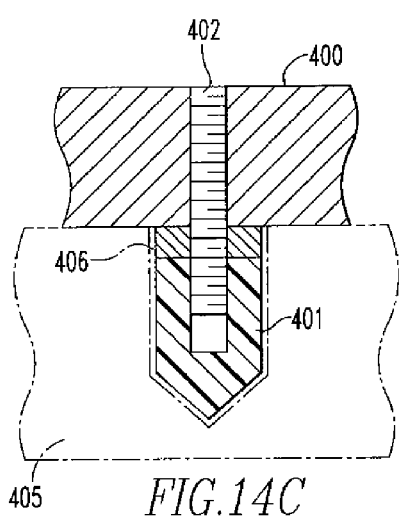
Figure 14D:
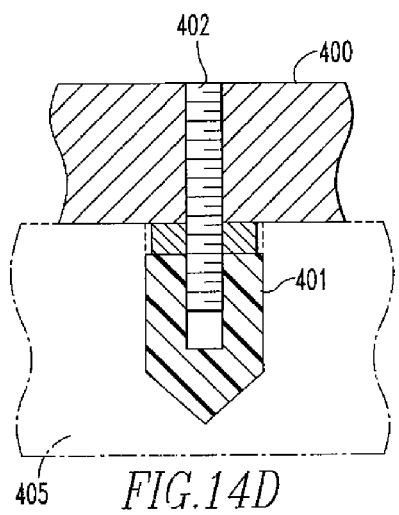

FIG. 13 shows a shoulder prosthesis 300 including a stem 301, a humeral component 302, and a glenoid component 303. The glenoid component 303, includes a fin 304 having a hole 305 extending therethrough. A shape memory polymer material 306 is coupled to the fin 304, such that the material 306 covers the hole 305. In use, the glenoid component 303 is inserted into the glenoid bone (not shown) and then the polymer material 306 is provided with energy to deform the material 306 and fixate the component 303 to the bone. In addition, the hole 305 allows for expansion of the polymer material 306 into the hole 305, thereby further fixating the material 306 to the component 303. Other surface features that would provide firm fixation of the material 306 to the component 303 after the material 306 was provided with energy, could also be used. The polymer material 306 may be in the form of a ring that slides over the fin 304 and covers both sides of the hole 305. Alternatively, the material 306 may be in the form of strips that may be located anywhere on the component 303. Furthermore, a sheath of shape memory polymer material may be placed over the entire glenoid component 303 or the component 303 may include alternating sections of a polymer material having shape memory qualities and a metal or non-metal material or a polymer material that does not have shape memory qualities. The stem 301, humeral component 302, and glenoid component 303 are coupled to one another via methods known to one of ordinary skill in the art.

FIGS. 14-16 show a tibial tray that includes members for further fixation of the tray 10 to the patient's proximal tibia. The members 401 may be coupled to the tray 400 in a variety of methods. FIG. 14A shows a threaded post 402 attached to the tray 400 at a first end 402a of the post 402 and a member 401 having a central opening 403. As shown in FIG. 14B, the member 401 is coupled to the threaded post 402 by placing the opening 403 over a second end 402b of the post 402. The opening 403 includes a diameter that allows the opening 403 to have an interference fit with the post 402. The member 401 includes a shape memory polymer material. As shown in FIG. 14C, upon placing the tray 400 on the proximal tibia 405, the member 401 is placed within a hole 406 in the tibia 405. After placement of the tray 400 on the tibia 405, the polymer material is provided with energy to expand the material and allow the material to engage with the bone 405, as shown in FIG. 14D.

Figure 15A:
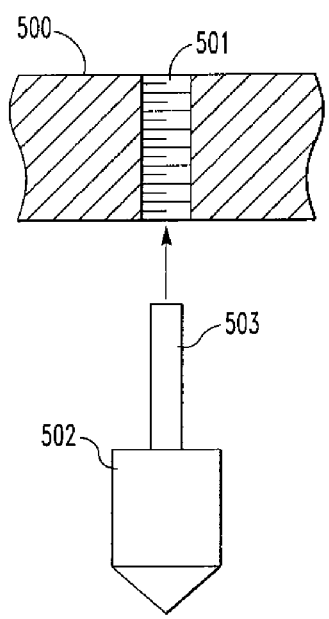
FIGS. 15A-D show a perspective view of an eleventh embodiment of a tibial tray of the present disclosure.
Figure 15B:
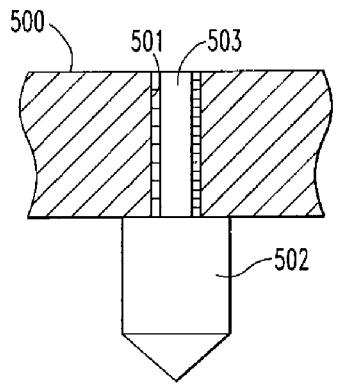
Figure 15C:
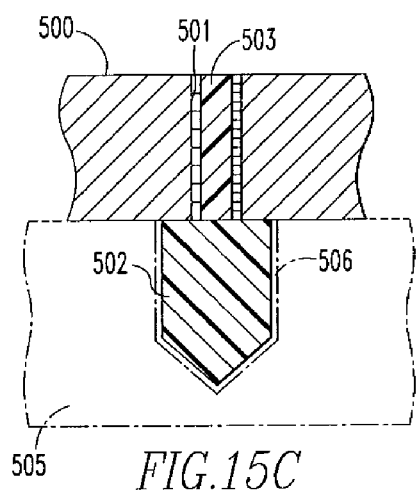
Figure 15D:
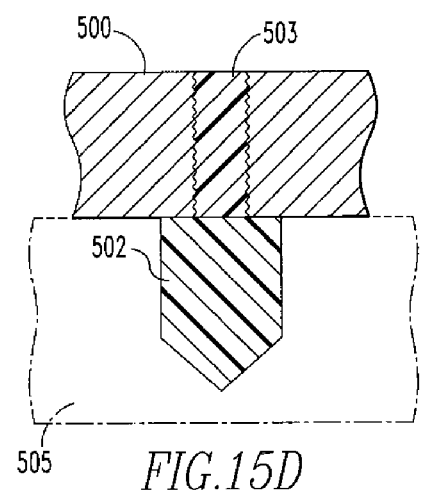

FIG. 15A shows a tray 500 having a threaded opening 501 and a member 502 having a connector 503. As shown in FIG. 15B, the member 502 is coupled to the tray 500 by inserting the connector 503 into the opening 501. The connector 503 includes a diameter that allows the connector 503 to have an interference fit with the threaded opening 501. As shown in FIG. 15C, upon placing the tray 500 on the proximal tibia 505, the member 502 is placed within a hole 506 in the tibia 505. After placement of the tray 500 on the tibia 505, the polymer material is provided with energy to expand the material and allow the material to engage with the bone 505, as shown in FIG. 15D.

Figure 16A:
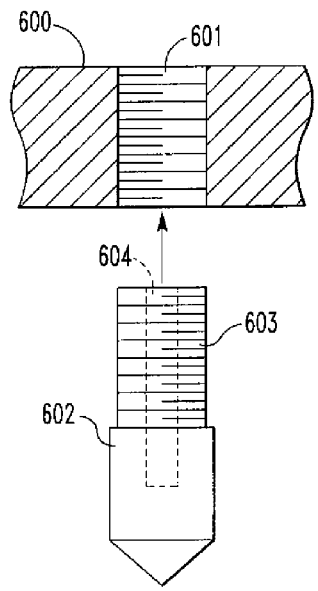
FIGS. 16A-D show a perspective view of a twelfth embodiment of a tibial tray of the present disclosure.
Figure 16B:
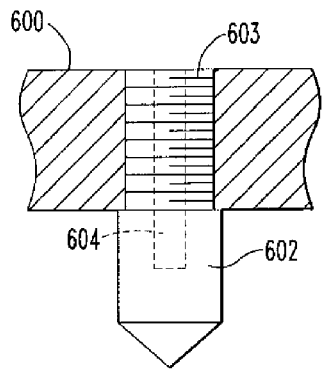
Figure 16C:
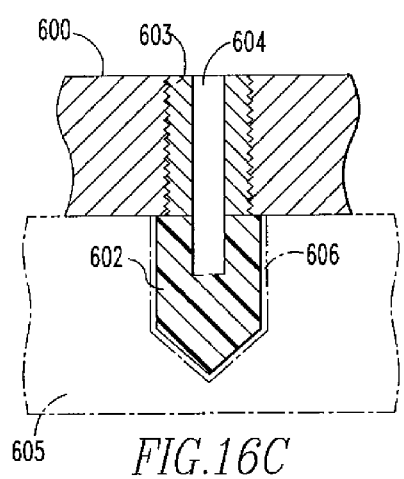
Figure 16D:
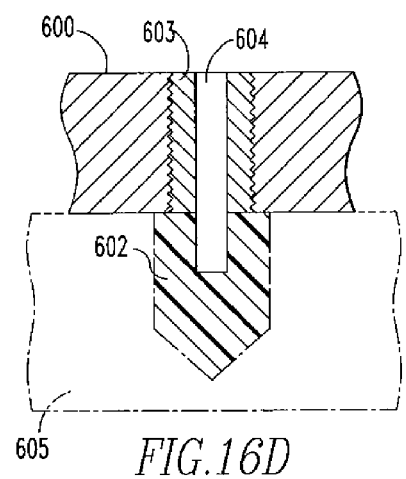

FIG. 16A shows a tray 600 having a threaded opening 601 and a member 602 having a threaded connector 603 and an aperture 604. As shown in FIG. 16B, the member 602 is coupled to the tray 600 by rotary advancement of the threaded connector 603 into the threaded opening 601. As shown in FIG. 16C, upon placing the tray 600 on the proximal tibia 605, the member 602 is placed within a hole 606 in the tibia 605. After placement of the tray 600 on the tibia 605, the polymer material is provided with energy to expand the material and allow the material to engage with the bone 605, as shown in FIG. 16D. The polymer material may be provided with energy, in the form of thermal energy, by placing a heating device, such as a cauterizing device, within the aperture 604. Other methods of providing energy, as described above, may also be used.

Figure 17:
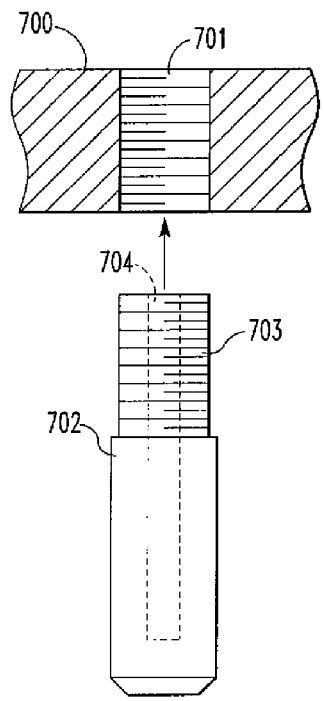
FIG. 17 shows a perspective view of a thirteenth embodiment of a tibial tray of the present disclosure.
Figure 18A:
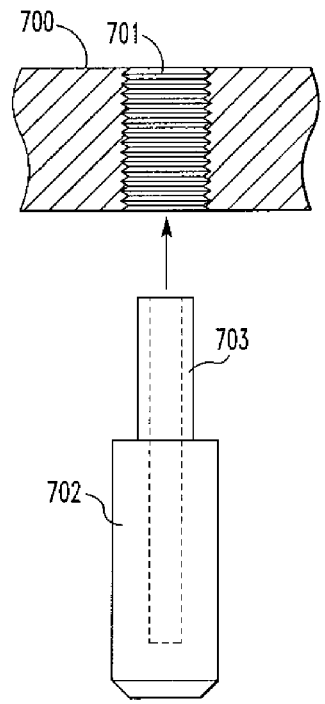
FIGS. 18A-C show a perspective view of a fourteenth embodiment of a tibial tray of the present disclosure.
Figure 18B:
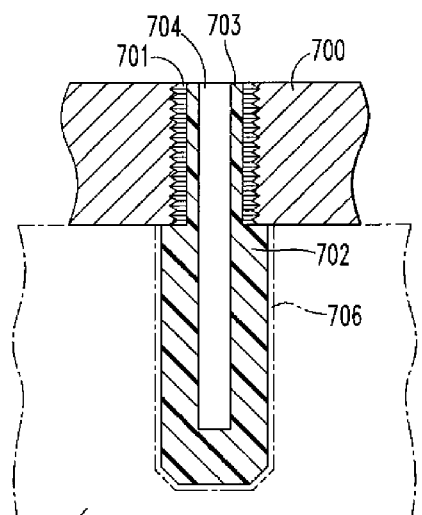
Figure 18C:
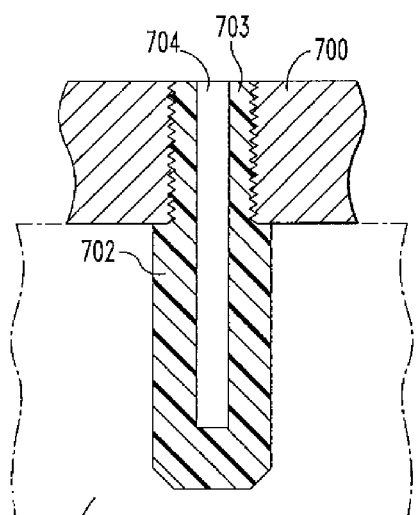

FIG. 17 shows a tray 700 having a threaded opening 701 and a fixator 702 having a threaded connector 703 and an aperture 704. FIG. 18A shows the fixator 702 of FIG. 17 having a connector 703 without threads. The fixator 702 is coupled to the tray 700 by either rotary advancement or interference fit of the connector 703, of FIG. 17 or FIG. 18A, respectively, into the threaded opening 701. As shown in FIG. 18B, upon placing the tray 700 on the proximal tibia 705, the fixator 702 is placed within a hole 706 in the tibia 705. After placement of the tray 600 on the tibia 705, the polymer material is provided with energy to expand the material and allow the material to engage with the bone 705, as shown in FIG. 18C. The polymer material may be provided with energy, in the form of thermal energy, by placing a heating device, such as a cauterizing device, within the aperture 704. Other methods of providing energy, as described above, may also be used.

Figure 19:
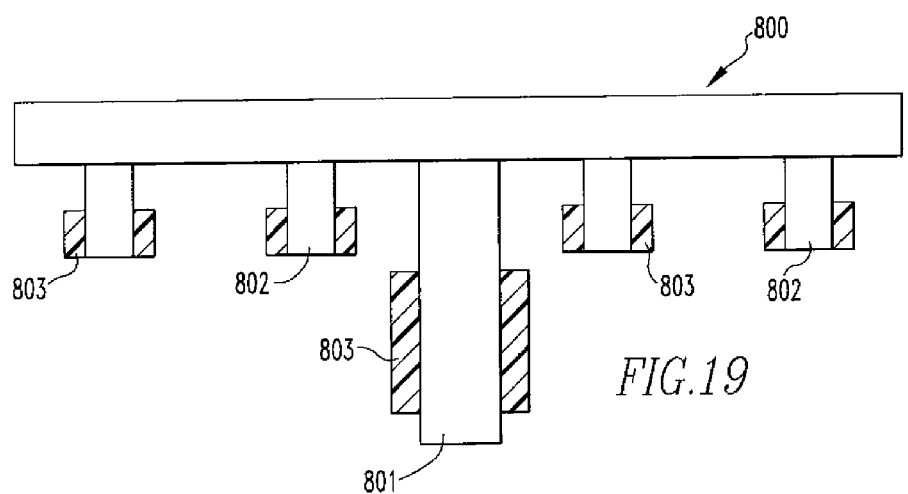
FIG. 19 shows a perspective view of a fifteenth embodiment of a tibial tray of the present disclosure.

FIG. 19 shows a tibial tray 800 having metal posts 802 and a metal fixator 801 coupled to the tray 800. Cylindrical sleeves of biaxially oriented shape memory polymer material 803 are coupled to the posts 802 and the fixator 801. Structurally, the sleeves 803 are similar to the sleeves 20 described above. After placement of the tray 800 on a tibia, the polymer material 803 is provided with energy to increase the outer diameter and decrease the inner diameter, ensuring that during relaxation the shape memory polymer material remains fixed to the metal posts 802 and fixator 801 while fixating the tray 800 onto the bone.

Figure 20:
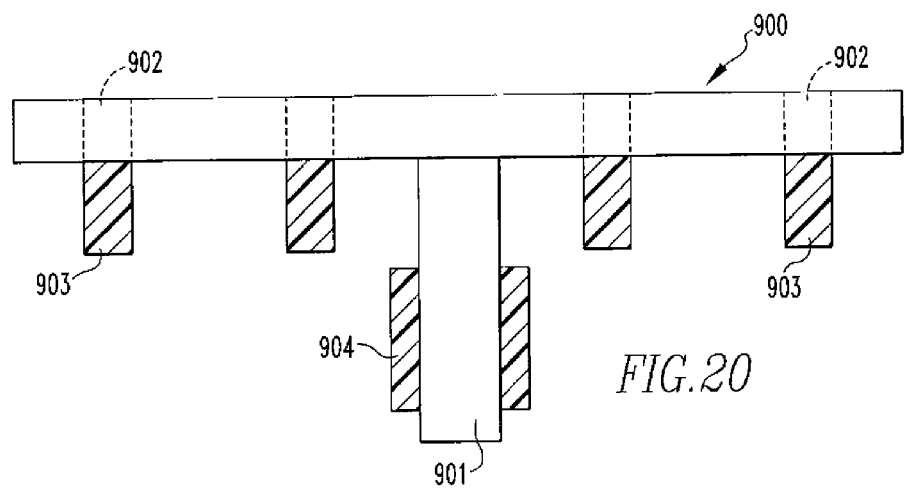
FIG. 20 shows a perspective view of a sixteenth embodiment of a tibial tray of the present disclosure.

FIG. 20 shows a tibial tray 900 having a metal fixator 901 and openings 902. Rods of uniaxially oriented shape memory polymer material 903 are disposed within the openings 902 and a sleeve of biaxially oriented shape memory polymer material 904 is coupled to the fixator 901. After placement of the tray 900 on a tibia, the polymer material 903,904 is provided with energy to fixate the tray 900 onto the bone.

A uniaxially oriented shape memory polymer sleeve has both an internal diameter and an external diameter that increase when the sleeve is provided with energy. After deformation of the sleeve, the final wall thickness of the sleeve is approximately constant. If a gap between the bone and the fixation device is greater than this sleeve wall thickness, then the sleeve may not lock the device in place. In contrast, a biaxially oriented shape memory polymer sleeve has an internal diameter that decreases and an external diameter that increases when the sleeve is provided with energy. This allows for the internal diameter to grip the sleeve to the post or fixator and the outer diameter to engage the surrounding bone, thereby locking the device in place. In order to make a sleeve of biaxially oriented shape memory polymer material, a rod of shape memory polymer material may be die drawn over a mandrel. Further discussion of this process can be found in U.S. Patent Application Ser. No. 60/912,740, the disclosure of which is incorporated herein by reference in its entirety.

Figure 21:
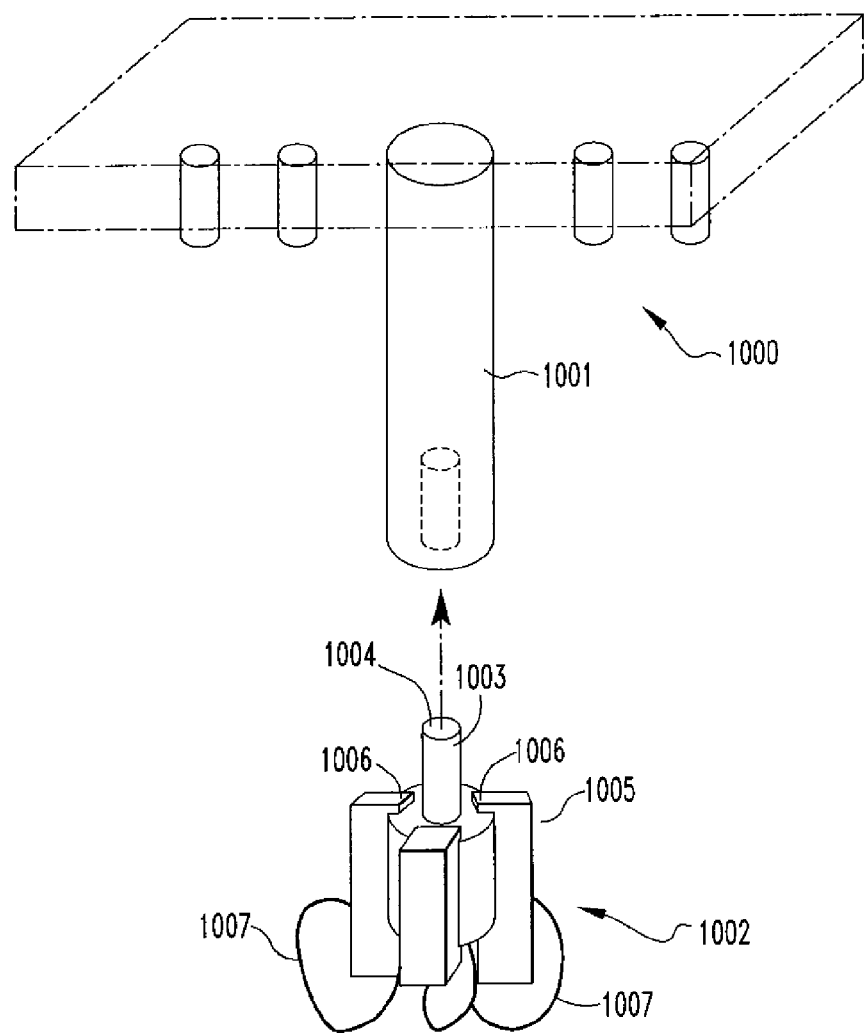
FIG. 21 shows a perspective view of a seventeenth embodiment of a tibial tray of the present disclosure.

FIG. 21 shows a tibial tray 1000 similar to the tray 900 shown in FIG. 20. The fixator 1001 includes a shape memory polymer assembly 1002. The assembly 1002 includes a member 1003 having a connector 1004 coupled to the fixator 1001 and blocks 1005 coupled to the member 1003. The member 1003 includes a first shape memory polymer material having a first relaxation temperature and the blocks 1005 include a second shape memory polymer material having a second relaxation temperature. The blocks 1005 are coupled to the member 1003 via an interference fit with the channels 1006 and via flexible members 1007, such as sutures. After placement of the tray 1000 on a tibia, the blocks 1005 are provided with energy to relax the blocks 1005 and allow the blocks 1005 to engage with the bone, thereby fixating the tray 1000 to the bone. In order to remove the tibial tray 1000, the member 1003 is provided with energy to relax the member 1003, thereby disengaging the member 1003 from the blocks 1005. Upon disengagement, the tray 1000 can be removed from the tibia 1000. Upon removal, the sutures 1007 become taught and pull out the blocks 1005.

Figure 22:
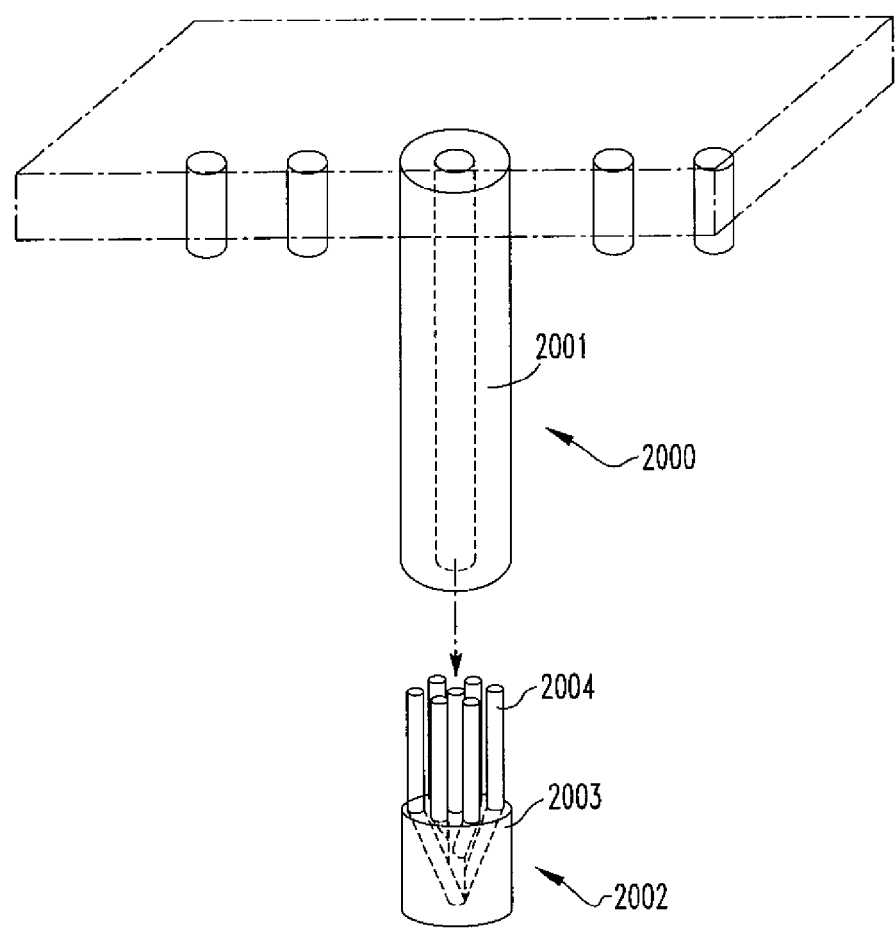
FIG. 22 shows a perspective view of an eighteenth embodiment of a tibial tray of the present disclosure.

FIG. 22 shows a tibial tray 2000 similar to the tray 1000 shown in FIG. 20. The fixator 2001 includes a shape memory polymer assembly 2002. The assembly 2002 includes a member 2003 having tubes or channels 2004 coupled to the fixator 2001. The member 2003 includes a shape memory polymer material. The tubes 2004, which may be metal, plastic, or other material known to one of skill in the art, can facilitate the passage of heating fluid through the member 2003, thereby causing relaxation of the member 2003 and fixation of the tray 2000 to the tibia. The tubes 2004 may be filled with heating fluid prior to implantation of the tray 2000 into the tibia or the fixator 2001 may be cannulated to allow for the passage of the heating fluid through the fixator 2001, through the channels 2004, and into the member 2003.

EXAMPLES

Figure 23:
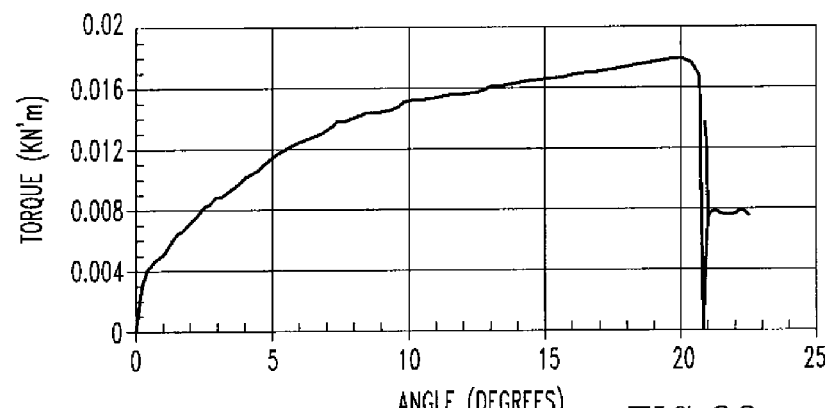
FIG. 23 shows a graph reflecting results of torsion testing performed on a tibial tray of the present disclosure.

A shape memory polymer rod, about 13 mm in diameter and about 100 mm in length, was inserted into ovine bone with about 20 mm of the rod protruding from the bone. The bone was immersed in water at 80° C. to heat the polymer. The portion of the rod protruding from the bone was not in the water and was therefore not heated. The bone was removed from the water after 5 minutes and left to cool to room temperature. Once at room temperature, the bone was gripped in a vice and the portion of the rod protruding from the bone was clamped into the top grip of a servohydrolic Instron in preparation for a torsion test. Torsion testing was carried at a constant angular displacement rate of 10 degrees/min. As can be seen in the graph of FIG. 23, a maximum torsion value of 18 Nm was recorded at an angle of 20°.

Figure 24:
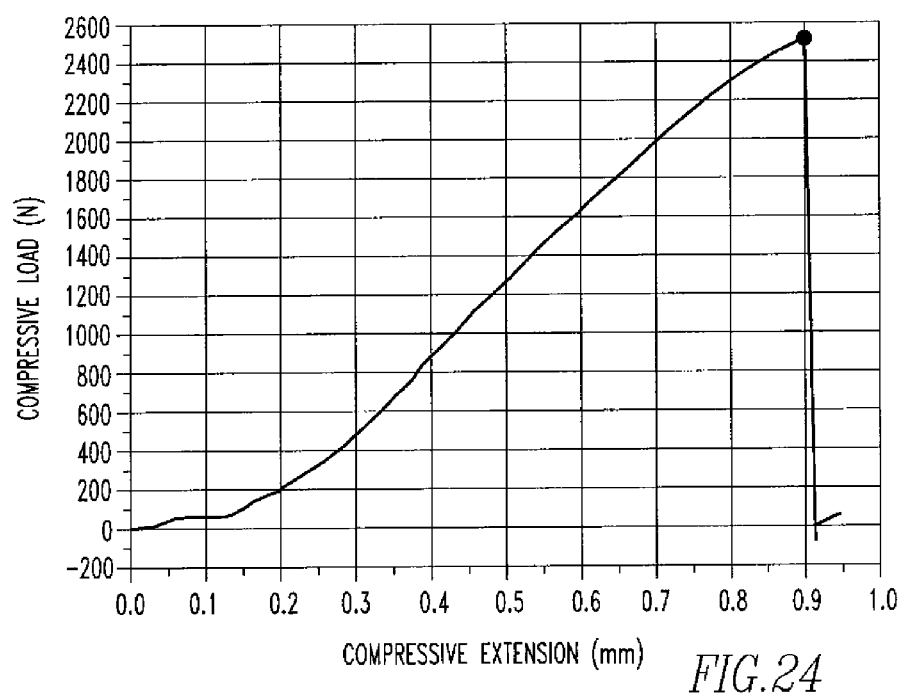
FIG. 24 shows a graph reflecting results of push-out testing performed on a tibial tray of the present disclosure.

A shape memory polymer rod, 13 mm in diameter and 25 mm in length, was inserted into ovine bone. The polymer rod had a hole of 4.76 mm drilled through the center. A stainless steel tube, having the same length as the polymer rod and with an outer diameter similar to the internal diameter of the polymer rod, was inserted into the hole. A heating probe, having a 4 mm diameter and controlled by a DC power supply, was inserted inside the stainless steel tube. The power supply and control unit were then used to set the probe to heat at temperatures ranging from 175° C. to 190° C. for a maximum duration of 25 minutes. Once the heating was stopped, the polymer rod was left to cool to room temperature before mechanical push-out tests were carried out. During all mechanical push-out tests, the polymer rod was pushed towards the widest end of the bone at a rate of 1 mm/minute. As can be seen in the graph of FIG. 24, a maximum push-out value of 2505N was recorded.

A tibial tray having metal posts and a shape memory polymer fixator and a tibial tray having shape memory polymer posts and a shape memory polymer fixator were both implanted into 20 pcf synthetic test bone (sawbone). Fixation of the trays into the sawbone was achieved by heating the shape memory polymer material using hot water at 70° C. for 10 minutes. The samples were left to cool to room temperature prior to mechanical testing. Mechanical testing was performed on an Instron. Each tray was clamped in place and a tensile mechanical test was performed to pull the trays out of the sawbone block. The Instron was set up at a displacement of 1 mm per minute and the forces throughout the experiment were recorded. The test ended when fixation failed. The tibial tray having metal posts and a shape memory polymer fixator had a pull-out value of 525 N and the tibial tray having shape memory polymer posts and a shape memory polymer fixator had a pull-out value of 960 N.

Figure 25:
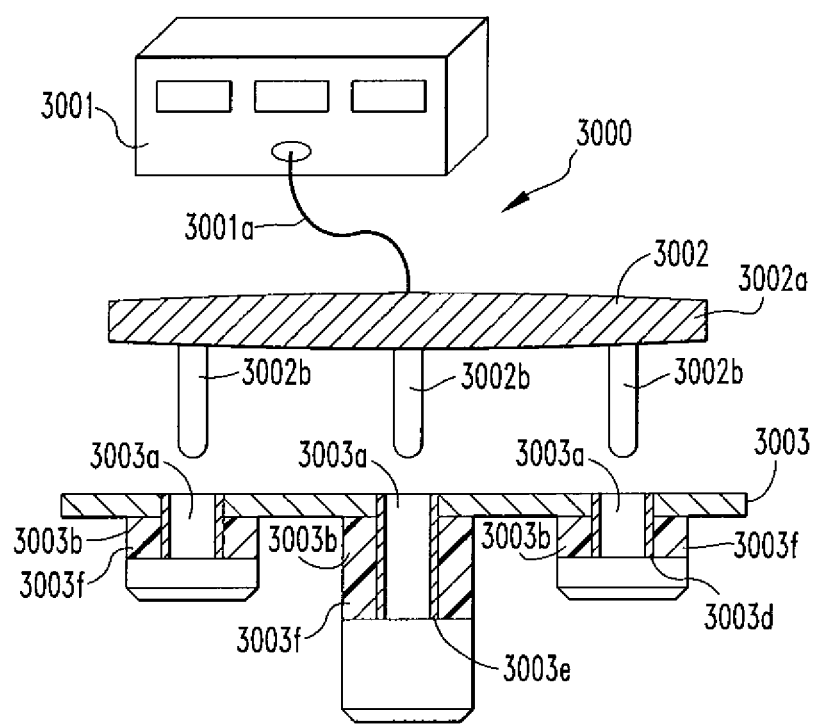
FIG. 25 shows a multiple heater probe system of the present disclosure.

FIG. 25 shows a multiple heater probe system 3000 for activating multiple shape memory polymer components in a single medical device. The heating system 3000 includes a control unit 3001 linked to a heating device 3002 via an electrical connection 3001a. The control unit 3001 may include, without limitation, a digitally controlled potentiometer, electronic thermistor, electronic thermostat, or other temperature control unit known to one of skill in the art. The heating device 3002 includes a main body 3002a, such as a cartridge heater, and one or more heating probes 3002b coupled to the body 3002b, which mate with holes 3003a in a tibial tray 3003, as will be further described below. The probes 3002b may be made of a metal, alloy, ceramic, or any other thermo conductive material.

In the embodiment shown, the tibial tray 3003 includes metal posts 3003d and a metal fixator 3003e coupled to the tray 3003. Sleeves 3003b, including both metal components 3003c and shape memory polymer components 3003f, are coupled to the posts 3003d and fixator 3003e. The shape memory polymer component 3003f is adjacent to the posts 3003d and fixator 3003e to ensure sufficient heat transfer from the probes 3002b to the shape memory polymer component 3003f.

In use, the tibial tray 3003 is placed in bone that has been shaped to accept the tray 3003. The heating device 3002 is then placed on the tray 3003, such that the probes 3002b are disposed within the posts 3003d and fixator 3003e, and the control unit 3001 is turned on to provide the probes 3002a, and therefore the shape memory polymer components 3003f, with heat at an appropriate temperature and for an appropriate duration of time until the tray 3003 is firmly fixed within the bone. The temperature and duration of time are dependent on a variety of factors including, without limitation, the type of material and the amount of fixation.

FIGS. 26A and 26B show a tibial tray 4000 which incorporates a sleeve of shape memory polymer material 4004 on a metal fixator 4006. The fixator 4006 includes an area of reduced diameter 4006a where the shape memory polymer sleeve 4004 is positioned so that the sleeve 4004 sits flush with the rest of the fixator 4006. Within the area of reduced diameter 4006a, an integral heating coil circuit 4003 is located. A removable electrical connection 4001 and connector plug 4002 couple the coil 4003 to a control unit, similar to the control unit shown in FIG. 25. The connector plug 4002, which may be a pin and socket connector, conductive, or other type of male/female connector, allows for an electrical current from the control unit to be conducted across the connection 4001 and delivered to the coil circuit 4003. The tibial tray 4000 is placed into bone shaped to accept it and the fixator 4006. The tray 4000 is coupled to the control unit via the electrical connection 4001 and the heating process is initiated. The coil 4003 heats the sleeve 4004 causing it to expand, as shown by the arrows in FIG. 26B, and lock the tray 4000 into the bone. When the heating process is complete, the electrical connection 4001 and connector plug 4002 may be removed leaving a connector port (not shown), which can be sealed by an appropriate covering material, such as a plug or screw.

Similar to FIGS. 26A-26B, FIGS. 27A-27B FIGS. 26A and 26B show a tibial tray 4000 which incorporates a sleeve of shape memory polymer material 4004 on a metal fixator 4006. The fixator 4006 includes an area of reduced diameter 4006a where the shape memory polymer sleeve 4004 is positioned so that the sleeve 4006 sits flush with the rest of the fixator 4006. However, the electrical coil 4003 is contained within the sleeve of shape memory polymer material 4004, rather than being contained within the area of reduced diameter 4006a. A removable electrical connection 4001 and connector plug 4002 couple the coil 4003 to a control unit, similar to the control unit shown in FIG. 25. The connector plug 4002, which may be a pin and socket connector, conductive, or other type of male/female connector, allows for an electrical current from the control unit to be conducted across the connection 4001 and delivered to the coil circuit 4003. The tibial tray 4000 is placed into bone shaped to accept it and the fixator 4006. The tray 4000 is coupled to the control unit and the heating process is initiated. The coil 4003 heats the sleeve 4004 causing it to expand, as shown by the arrows in FIG. 26B, and lock the tray 4000 into the bone. When the heating process is complete, the electrical connection 4001 and connector plug 4002 may be removed leaving a connector port (not shown), which can be sealed by an appropriate covering material, such as a plug or screw.

Figure 28A:
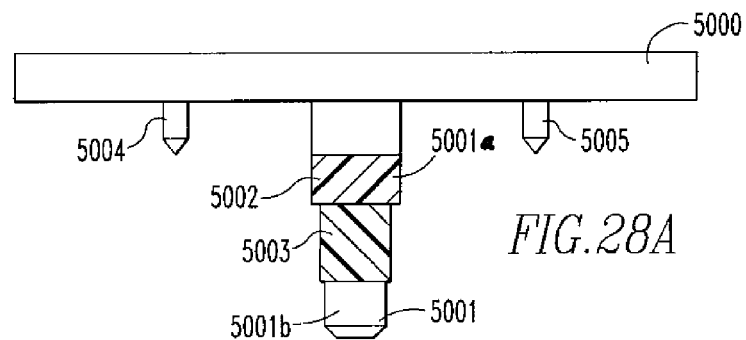
FIGS. 28A-28C show front views of a twenty-first embodiment of a tibial tray of the present disclosure.
Figure 28B:
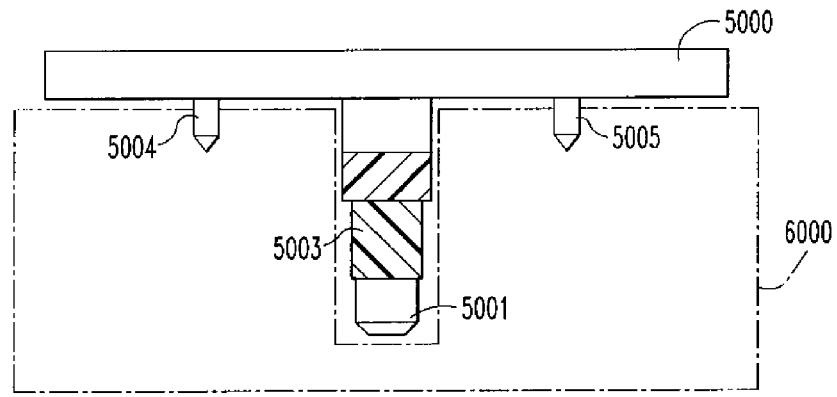
Figure 28C:
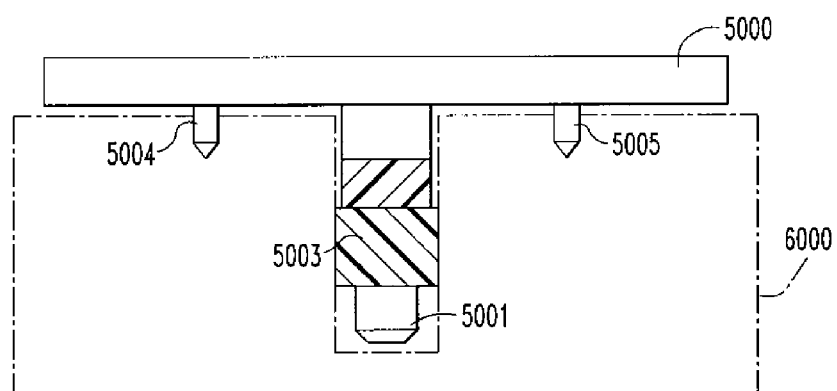

FIGS. 28A-28C show a tibial tray 5000 including posts 5004,5005 and a fixator 5001 having a first component 5001a including a sleeve of non-shape memory polymer material 5002 and a second component 5001b, coupled to the first component 5001, and including a sleeve of shape memory polymer material 5003. The sleeve of non-shape memory polymer material 5002 includes biological agents and/or bioactives for delivery to surrounding tissue when the tray 5000 is placed in bone, as will be further described below. The biological agents and/or bioactives may include, without limitation, cells, proteins, peptides, growth factors, cytokines, antibiotics, and antimicrobials. The sleeve of non-shape memory polymer 5002 may be porous in structure to increase the surface area and facilitate improved loading of the agent/active. In addition, delivery of the active/agent may be controlled by making the sleeve 5002 out of a a resorbable polymer material or a composite of both resorbable and non-resorbable polymers.

As shown in FIGS. 28B-28C, the tibial tray 5000 is placed into bone 6000 shaped to accept it, the fixator 5001, and the posts 5004,5005. The sleeve 5003 is then provided with energy, via one of the methods described above or another method known to one of skill in the art, to deform the sleeve 5003, as shown in FIG. 28C, and fixate the tray 5000 to the bone 6000.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting.

Thus, the breadth and scope of the present disclosure should not be limited by any of the above-described exemplary embodiments, but should be defined only in accordance with the following claims appended hereto and their equivalents.

What is claimed is:

1. A tibial tray for a knee prosthesis comprising:
at least one fixator extending from a distal surface of the tray and configured for insertion into an opening in a patient's proximal tibia bone for holding the tray on the tibia bone;
a polymer material attached to an exterior peripheral surface of the fixator and positioned for engagement within the opening in the tibia bone for fixation of the tray to the tibia bone, wherein the polymer material is positioned along a length of the fixator and includes an outer bone engagement surface; and
means for outwardly expanding the polymer material within the opening in the tibia bone and for engaging the outer bone engagement surface of the polymer material against the tibia bone to thereby fixate the tray to the tibia bone.

2. The tibial tray of claim 1 wherein the tray includes multiple fixators.

3. The tibial tray of claim 1 wherein the exterior surface of the fixator includes an interface portion, the polymer material coupled to the interface portion.

4. The tibial tray of claim 3 wherein the interface portion is a shaped interface portion.

5. The tibial tray of claim 1 wherein the fixator comprises an upper portion and a lower portion, the upper portion extending distally from the distal surface of the tray and the lower portion extending distally from the upper portion and being releasably coupled to the upper portion, the polymer material located between the upper portion and the lower portion.

6. The tibial tray of claim 1 wherein the fixator is releasably coupled to a distal surface of the tibial tray.

7. The tibial tray of claim 1 further comprising a locking member located on a proximal surface of the tibial tray, the locking member extending perpendicular to the proximal surface.

8. The tibial tray of claim 7 wherein the locking member includes a shape memory polymer material.

9. The tibial tray of claim 1, wherein the polymer material is selected from a group consisting essentially of an amorphous polymer, a semi-crystalline polymer, and combinations thereof.

10. The tibial tray of claim 1 wherein the polymer material comprises a sleeve extending about the exterior peripheral surface of the fixator.

11. The tibial tray of claim 10 wherein the sleeve has an overall length dimension extending along the length of the fixator, the sleeve having an overall width dimension less than the overall length dimension.

12. The tibial tray of claim 1 wherein the polymer material comprises a shape memory polymer material; and
wherein the means for outwardly expanding and engaging comprises an application of heat to the shape memory polymer material.

13. The tibial tray of claim 1 wherein the means for outwardly expanding and engaging does not include compression of the polymer material.

14. A femoral component for a knee prosthesis comprising:
at least one femoral condyle;
at least one peg configured for insertion into an opening in a patient's distal femur bone for holding the femoral component on the femur bone, the peg located on a proximal surface of the femoral condyle;
a polymer material attached to an exterior peripheral surface of the peg and positioned for engagement within the opening in the femur bone for fixation of the femoral component to the femur bone, wherein the polymer material is positioned along a length of the peg and includes an outer bone engagement surface; and
means for outwardly expanding the polymer material within the opening in the femur bone and for engaging the outer bone engagement surface of the polymer material against the femur bone to thereby fixate the femoral component to the femur bone.

15. The femoral component of claim 14 wherein the polymer material is selected from a group consisting essentially of an amorphous polymer, a semi-crystalline polymer, combinations thereof, a copolymer, and a polymer blend.

16. The femoral component of claim 14 wherein the polymer material comprises a sleeve extending about the exterior peripheral surface of the peg.

17. The femoral component of claim 16 wherein the sleeve has an overall length dimension extending along the length of the peg, the sleeve having an overall width dimension less than the overall length dimension.

18. The femoral component of claim 14 wherein the polymer material comprises a shape memory polymer material; and
wherein the means for outwardly expanding and engaging comprises an application of heat to the shape memory polymer material.

19. The femoral component of claim 14 wherein the means for outwardly expanding and engaging does not include compression of the polymer material.

20. A knee prosthesis comprising:
the tibial tray of claim 1; and
a femoral component, the femoral component including at least one femoral condyle having at least one peg configured for insertion into an opening in the patient's distal femur bone for holding the femoral component on the femur bone, the peg located on a proximal surface of the femoral condyle;
a polymer material attached to an exterior peripheral surface of the peg and positioned for engagement within the opening in the femur bone for fixation of the femoral component to the femur bone, wherein the polymer material is positioned along a length of the peg and includes an outer bone engagement surface; and
means for outwardly expanding the polymer material within the opening in the femur bone and for engaging the outer bone engagement surface of the polymer material against the femur bone to thereby fixate the femoral component on the femur bone.

21. The knee prosthesis of claim 20 further comprising:
a tibial insert having a proximal surface that is shaped to engage the femoral component, the insert having a distal surface that fits against a proximal surface of the tibial tray;
a first locking member located on the proximal surface of the tibial tray; and
a second locking member located on a distal surface of the tibial insert, the first locking member of the tibial tray engaging the second locking member of the tibial insert.

22. The knee prosthesis of claim 21 wherein a shape memory polymer material is positioned between and engaged with both the first locking member of the tibial tray and the second locking member of the tibial insert.

23. The knee prosthesis of claim 20, wherein the polymer material is selected from a group consisting essentially of an amorphous polymer, a semi-crystalline polymer, combinations thereof, a copolymer, and a polymer blend.

* * * * *